United States Patent [19]
Ottow et al.

[11] Patent Number: 5,523,298
[45] Date of Patent: Jun. 4, 1996

[54] PROGESTATIONALLY ACTIVE 19,11-BRIDGED 4-ESTRENES

[75] Inventors: Eckhard Ottow; Wolfgang Schwede; Wolfgang Halfbrodt; Karl-Heinrich Fritzemeier; Rolf Krattenmacher, all of Berlin, Germany

[73] Assignee: Schering Aktiengesellschaft, Berlin, Germany

[21] Appl. No.: 135,486

[22] Filed: Oct. 13, 1993

[30] Foreign Application Priority Data

Oct. 13, 1992 [DE] Germany .................. 42 35 220.7

[51] Int. Cl.⁶ .................. C07J 53/00; A61L 31/56
[52] U.S. Cl. .................. 514/177; 514/178; 552/510; 552/513; 552/508
[58] Field of Search .................. 552/510, 513, 552/508; 514/177, 178

[56] References Cited

U.S. PATENT DOCUMENTS 5,095,129  3/1992  Ottow et al. .................. 552/510

OTHER PUBLICATIONS

CA110: 95627 (DE 3708942 Sep. 29, 1988) 1988.
CA114: 122839 (EP 399632 Nov. 28, 1990) 1990.
CA117: 131437 (DE 4038128 Jun. 4, 1992) 1992.

Primary Examiner—Gary Geist
Assistant Examiner—Catherine Kilby Scalzo
Attorney, Agent, or Firm—Millen, White, Zelane, & Branigan

[57] ABSTRACT

In this invention, the new etheno- and ethano-19,11-bridged 4-estrenes of general formula I

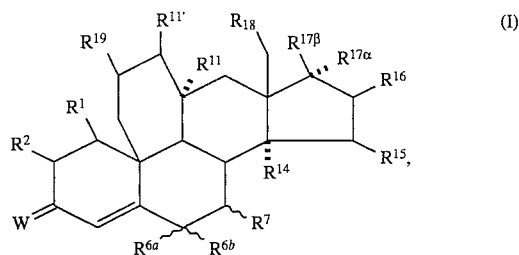

are described, in which W, $R^1$, $R^2$, $R^{6a}$, $R^{6b}$, $R^7$, $R^{14}$, $R^{15}$, $R^{16}$, $R^{11}$, $R^{11'}$ and $R^{19}$ have the meaning indicated in the description, as well as a process for their production.

The new compounds have strong progestational activity and are suitable for the production of pharmaceutical agents.

10 Claims, No Drawings

PROGESTATIONALLY ACTIVE 19,11-BRIDGED 4-ESTRENES

SUMMARY OF THE INVENTION

This invention relates to 19,11-bridged 4-estrenes of general formula I (I)

in which

W stands for an oxygen atom, the hydroxyimino >N—OH or two hydrogen atoms, $R^1$ and $R^2$ each stand for a hydrogen atom or together form group an additional bond or for a methylene bridge in α-position, $R^{6a}$ and $R^{6b}$ each stand for a hydrogen atom or together form a methylene group of a three-membered ring formed together with carbon atom 6, and $R^7$ in these cases means a hydrogen atom or $R^{6a}$ stands for a hydrogen atom or a fluorine, chlorine, bromine of iodine atom of for a straight-chain or branched-chain, saturated alkyl radical in α- or β-position with up to 4 carbon atoms, and then $R^{6b}$ and $R^7$ each represent a hydrogen atom or together an additional bond, or $R^{6b}$ and $R^7$ together stand for a methylene bridge in α- or β-position, and $R^{6a}$ is then a hydrogen atom, $R^7$ stands for a straight-chain or branched-chain, saturated alkyl radical in α- or β-position with up to 4 carbon atoms or for a thio group —$SR^{20}$, in which $R^{20}$ represents a hydrogen atom or an alkanoyl group with 1 to 4 carbon atoms, $R^{14}$, $R^{15}$ and $R^{16}$ each stand for a hydrogen atom or $R^{14}$ stands for a hydrogen atom in α-position and $R^{15}$ and $R^{16}$ together stand for an additional bond or for a methylene bridge in α- or β-position, or $R^{14}$ and $R^{15}$ each stand for a hydrogen atom and $R^{16}$ stands for a $C_1$–$C_4$ alkyl group in α- or β-position or $R^{16}$ together with $R^{17\alpha}$ stand for a methylene bridge in α-position and stands for a group $$-\underset{\underset{O}{\|}}{C}-R^{22}$$

$R_{16}$ stands for a hydrogen atom and $R^{14}$ and $R^{15}$ together stand for an additional bond, $R^{11}$, $R^{11'}$ and $R^{19}$ each stand for a hydrogen atom or $R^{11}$ stands for a hydrogen atom in α-position, and $R^{11'}$ and $R^{19}$ together stand for an additional bond or $R^{19}$ stands for a hydrogen atom and $R^{11}$ and $R^{11'}$ together stand for an additional bond, $R^{17\beta}/R^{17\alpha}$ means
—$OR^{21}$/—$(CH_2)_m$—A
—$OR^{21}$/—$(CH_2)_m$—C≡C—B
—$OR^{21}$/—$(CH_2)_p$—CH=CH—$(CH_2)_k$—D
—$OR^{21}$/—HC=C=CEG
—$OR^{21}$/—$CF_3$ $$-\underset{\underset{O}{\|}}{C}-R^{22}/-OR^{23}$$

$$-\underset{\underset{O}{\|}}{C}-R^{22}/-C_1-C_4\text{ alkyl}$$

$$-\underset{\underset{O}{\|}}{C}-R^{22}/-F$$

or $R^{17\beta}/R^{17\alpha}$ together mean with x = 1 or 2 with U = O or ⟨OH, H⟩ with $R^{21}$ and $R^{23}$ meaning a hydrogen atom, a $C_1$–$C_4$ alkyl or a $C_1$–$C_4$ alkanoyl group, $R^{22}$ meaning a $C_1$–$C_3$ alkyl group, A meaning a hydrogen atom, the cyano group, —$COOR^{24}$ or —$OR^{25}$ in which $R^{24}$ stands for $C_1$–$C_4$ alkyl and $R^{25}$ stands for hydrogen, $C_1$–$C_4$ alkyl or $C_1$–$C_4$ alkanoyl, B meaning a hydrogen atom, a $C_1$–$C_4$ alkyl group, a $C_2$ or $C_3$ alkinyl group, a fluorine, chlorine, bromine or iodine atom, a hydroxyalkyl, alkoxyalkyl or alkanoyloxyalkyl group with 1 to 4 carbon atoms each in the alkyl, alkoxy or alkanoyloxy part, D meaning a hydrogen atom, a hydroxy, $C_1$–$C_4$ alkoxy or $C_1$–$C_4$ alkanoyloxy group, E and G meaning hydrogen or $C_1$–$C_3$ alkyl, n meaning 0, 1, 2, 3 or 4, m meaning 0, 1 or 2, p meaning 0 or 1, k meaning 0, 1, 2 or 3 and $R^{18}$ stands for a hydrogen atom or a methyl group.

DETAILED DESCRIPTION OF THE PREFERRED EMBODIMENTS

Preferred according to this invention are those compounds of general formula I, in which W stands for an oxygen atom or two hydrogen atoms, $R^{6a}$ and $R^{6b}$ each stand for a hydrogen atom or for a three-membered ring formed together with carbon atom 6, or $R^{6a}$ stands for a chlorine or bromine atom or for a straight-chain, saturated $C_1$–$C_4$ alkyl radical in α- or β-position, or $R^{6b}$ and $R^7$ together stand for a methylene bridge in β-position or together for an additional double bond, or $R^7$ stands for a straight-chain or branched-chain, saturated alkyl radical in α- or β-position with up to 4 carbon atoms, $R^{14}$, $R^{15}$ and $R^{16}$ each stand for a hydrogen atom or $R^{14}$ stands for a hydrogen atom in α-position, and $R^{15}$ and $R^{16}$ together stand for an additional bond or for a methylene bridge in β-position, $R^{17\beta}/R^{17\alpha}$ mean
—OH/—$CH_3$;
—OC(O)$CH_3$/—$CH_3$;
—OH/—C≡CH,
—OC(O)$CH_3$/—C≡CH;
—OH/—C≡C—$CH_3$,
—OC(O)$CH_3$/—C≡C—$CH_3$;
—C(O)$CH_3$/—OC(O)$CH_3$

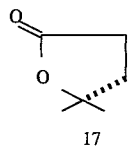

and the other substituents all can have the meanings indicated in formula I.

The compounds mentioned below are especially preferred according to the invention:

17-(Acetyloxy)-9,11α-dihydro-6'H-benzo[10,9,11]-19-norpregn-4-ene-3,20-dione;

17-(acetyloxy)-9,11α-dihydro-6-methyl-6'H-benzo[10,9,11]-19-norpregna-4,6-diene-3,20-dione;

17-(acetyloxy)-9,11α-dihydro-6α-methyl-6'H-benzo[10,9,11]-19-norpregn-4-ene-3,20-dione;

17-(acetyloxy)-6-chloro-9,11α-dihydro-6'H-benzo[10,9,11]-19-norpregna-4,6-diene-3,20-dione;

17-(acetyloxy)-6-chloro-1β,2β,9,11α-tetrahydro-3'H-cyclopropa[1,2][6"H]benzo[10,9,11]-19-norpregna-4,6-diene-3,20-dione;

17-(acetyloxy)-4',5',9,11α-tetrahydro-6'H-benzo[10,9,11]-19-norpregn-4-ene-3,20-dione;

17-(acetyloxy)-6-methyl-4',5',9,11α-tetrahydro-6'H-benzo[10,9,11]-19-norpregna-4,6-diene-3,20-dione;

17-(acetyloxy)-6-chloro-1β,2β,4",5",9,11α-hexahydro-3'H-cyclopropa[1,2][6"H]benzo[10,9,11]-19-norpregna-4,6-diene-3,20-dione;

17-(acetyloxy)-5',6'-dihydro-9H-benzo[10,9,11]-19-norpregn-4-ene-3,20-dione;

17-(acetyloxy)-5',6'-dihydro-6-methyl-9H-benzo[10,9,11]-19-norpregna-4,6-diene-3,20-dione;

17-(acetyloxy)-9,11α-dihydro-6'H-benzo[10,9,11]-18a-homo-19-norpregn-4-ene-3,20-dione;

17-(acetyloxy)-9,11α-dihydro-6-methyl-6'H-benzo[10,9,11]-18a-homo-19-norpregna-4,6-diene-3,20-dione;

9,11α-dihydro-17-methyl-6'H-benzo[10,9,11]-19-norpregn-4-ene-3,20-dione;

17-(acetyloxy)-9,11α-dihydro-6'H-benzo[10,9,11]-19-norpregna-4,6-diene-3,20-dione;

3',9,11α,16β-tetrahydrocyclopropa[16,17][6H]-benzo[10,9,11]-19-norpregn-4-ene-3,20-dione;

9,11α-dihydro-17-methyl-6'H-benzo[10,9,11]-18a-homo-19-norpregn-4-ene-3,20-dione;

3',9,11α,16β-tetrahydrocyclopropa[16,17][6H]-benzo[10,9,11]-18a-homo-19-norpregn-4-ene-3,20-dione;

9,11α-dihydro-17β-hydroxy-17α-methyl-6'H-benzo[10,9,11]estr-4-en-3-one;

9,11α-dihydro-17α-ethinyl-17β-hydroxy-6'H-benzo[10,9,11]estr-4-en-3-one;

9,11α-dihydro-17β-hydroxy-17α-(1-propinyl)-6'H-benzo[10,9,11]estr-4-en-3-one;

9,11α-dihydro-17β-hydroxy-17α-[1,3-pentadiinyl]-6'H-benzo[10,9,11]estr-4-en-3-one;

9,11α-dihydro-17β-hydroxy-17α-(3-hydroxy-1-propenyl)-6'H-benzo[10,9,11]estr-4-en-3-one;

9,11α-dihydro-17β-hydroxy-17α-(3-hydroxypropyl)-6'H-benzo[10,9,11]estr-4-en-3-one;

17β-hydroxy-17α-methyl-4',5',9,11α-tetrahydro-6'H-benzo[10,9,11]estr-4-en-3-one;

17α-ethinyl-17β-hydroxy-4',5',9,11α-tetrahydro-6'H-benzo[10,9,11]estr-4-en-3-one;

17β-hydroxy-17α-(1-propinyl)-4',5',9,11α-tetrahydro-6'H-benzo[10,9,11]estr-4-en-3-one;

5',6'-dihydro-17α-ethinyl-17β-hydroxy-9H-benzo[10,9,11]estr-4-en-3-one;

5',6'-dihydro-17β-hydroxy-17α-(1-propinyl)-9H-benzo[10,9,11]estr-4-en-3-one;

9,11α-dihydro-17α-ethinyl-17β-hydroxy-6'H-benzo[10,9,11]-18a-homoestr-4-en-3-one;

9,11α-dihydro-17β-hydroxy-17α-(1-propinyl)-6'H-benzo[10,9,11]-18a-homoestr-4-en-3-one;

17α-(1-butinyl)-9,11α-dihydro-17β-hydroxy-6'H-benzo[10,9,11]-18a-homoestr-4-en-3-one;

9,11α-dihydro-17α-(1,2-propadienyl)-17β-hydroxy-6'H-benzo[10,9,11]-18a-homoestr-4-en-3-one;

17α-ethinyl-17β-hydroxy-4',5',9,11α-tetrahydro-6'H-benzo[10,9,11]-18a-homoestr-4-en-3-one;

17β-hydroxy-17α-(1-propinyl)-4',5',9,11α-tetrahydro-6'H-benzo[10,9,11]-18a-homoestr-4-en-3-one;

5',6'-dihydro-17α-ethinyl-17β-hydroxy-9H-benzo[10,9,11]-18a-homoestr-4-en-3-one;

5',6'-dihydro-17β-hydroxy-17α-(1-propinyl)-9H-benzo[10,9,11]-18a-homoestr-4-en-3-one;

9,11α-dihydro-17α-ethinyl-17β-hydroxy-6'H-benzo[10,9,11]estra-4,15-dien-3-one;

9,11α-dihydro-17β-hydroxy-17β-(1-propinyl)-6'H-benzo[10,9,11]estra-4,15-dien-3-one;

17α-ethinyl-17β-hydroxy-4',5',9,11α-tetrahydro-6'H-benzo[10,9,11]estra-4,15-dien-3-one;

5',6'-dihydro-17α-ethinyl-17β-hydroxy-9H-benzo[10,9,11]estra-4,15-dien-3-one;

5',6'-dihydro-17β-hydroxy-17α-(1-propinyl)-9H-benzo[10,9,11]estra-4,15-dien-3-one;

9,11α-dihydro-17α-ethinyl-17β-hydroxy-6'H-benzo[10,9,11]-18a-homoestra-4,15-dien-3-one;

9,11α-dihydro-17β-hydroxy-17α-(1-propinyl)-6'H-benzo[10,9,11]-18a-homoestra-4,15-dien-3-one;

17α-ethinyl-17β-hydroxy-4',5',9,11α-tetrahydro-6'H-benzo[10,9,11]-18a-homoestra-4,15-dien-3-one;

5',6'-dihydro-17α-ethinyl-17β-hydroxy-9H-benzo[10,9,11]-18a-homoestra-4,15-dien-3-one;

5',6'-dihydro-17β-hydroxy-17α-(1-propinyl)-9H-benzo[10,9,11]-18a-homoestra-4,15-dien-3-one;

4",5",9,11α-tetrahydrospiro[6'H-benzo[10,9,11]estr-4-ene-17β,2"(3"H)-furan]-3-one;

3",4",9,11α-tetrahydrospiro[6'H-benzo[10,9,11]estr-4-ene-17β,2"(5"H)-furan]-3,5"-dione;

3"",4"", 6α,7α,9,11α,15α,16α-octahydrospiro[3'H-3"H-dicyclopropa[6,7:15,16]-[6H]benzo[10,9,11]estr-4-ene-17β,2"",(5""H)-furan]-3,5""-dione;

3"",4"",9',11'α,15'α,16'α-hexahydrospiro[cyclo-propane-1,6'-[3H]cyclopropane[15,16][6H]benzo[10,9,11]estr-4-ene-17'β,2""(5"")-furan]-3',5""-dione;

3"",4"",9',11'α,15'α,16'α-hexahydrospiro[cyclopropane-1,6'-[3H]cyclopropa[15,16]-[6H]benzo[10,9,11]estra-1,4-diene-17'β,2""(5""H)-furan]-3',5""-dione;

3"",4"",4"",5'",6α,7α,9,11α,15α,16α-decahydrospiro [3'H,3"H-dicyclopropa[6,7:15,16][6H]-benzo[10,9,11] estr-4-ene-17β,2""(5""H)-furan]-3,5""-dione;

3",4", 9,11α-tetrahydrospiro[6'H-benzo[10,9,11]-18a-homoestr-4-ene-17β,2"(5")-furan]-3,5"-dione;

3"",4"",6α,7α,9,11α,15α,16α-octahydrospiro-[3'H,3"H-dicyclopropa[6,7:15,16][6H]benzo[10,9,11]-18a-homoestr-4-ene-17β,2""(5""H)-furan]-3,5""-dione;

9,11α-dihydro-17α-ethinyl-6'H-benzo[10,9,11]estr-4-en-17β-ol;

17α-ethinyl-4',5',9,11α-tetrahydro-6'H-benzo[10,9,11] estr-4-en-17β-ol;

5',6'-dihydro-17α-ethinyl-9H-benzo[10,9,11]-estr-4-en-17β-ol;

9,11α-dihydro-17α-ethinyl-6'H-benzo[10,9,11]estra-4,15-dien-17β-ol;

9,11α-dihydro-17α-ethinyl-6'H-benzo[10,9,11]-18a-homoestr-4-en-17β-ol;

9,11α-dihydro-17α-ethinyl-6'H-benzo[10,9,11]-18a-homoestra-4,15-dien-17β-ol.

19,11β-Bridged steroids as the species structurally coming closest to the described compounds in question is brought out for the first time in DE-A 37 08 942 (EP-A 0 283 428). But the known compounds, unlike the compounds in question here, exhibit no etheno or ethano bridge between C11 and C19; rather, the two carbon atoms are bridged there by two adjacent carbon atoms of a generally substituted phenylene ring. Both the known compounds and also the compounds described here are distinguished by an extraordinarily high affinity to the progestin receptor.

In the progestin receptor bonding test for progestational activity by using cytosol from rabbit uterus homogenate and from $^3$H-progesterone as reference substance, the new compounds show a very great affinity to the progestin receptor and are greatly effective in the pregnancy maintenance test on the rat after subcutaneous administration.

In the following table, the competition factors ($K_F$) are indicated in the progestin receptor bonding test. Competition factor $K_F$ as a measurement for the bonding strength is defined as the ratio of the concentration of the test substance to the concentration of the standard (progesterone), in which both compounds show the same displacement of $^3$H-progesterone from the progesterone-receptor complex, so that a low $K_F$ value indicates great bonding strength (high affinity) (Table 1):

TABLE 1

Progestin Receptor Bonding Test

| Compound | $K_F$ (progestin) |
| --- | --- |
| A | 0.6 |
| B | 0.7 |
| C | 0.4 |
| D | 0.6 |
| E | 0.5 |
| F | 0.5 |
| G | 0.6 |
| H | 0.7 |
| I | 0.3 |
| K | 0.3 |
| L | 0.4 |

A: 9,11α-Dihydro-17α-ethinyl-17β-hydroxy-6'H-benzo [10,9,11]estr-4-en-3-one;

B: 9,11α-dihydro-17β-hydroxy-17α-(1-propinyl)-6'H-benzo[10,9,11]estr-4-en-3-one;

C: 9,11α-dihydro-17α-ethinyl-17β-hydroxy-6'H-benzo [10,9,11]estra-4,15-dien-3-one;

D: 9,11α-dihydro-17β-hydroxy-17α-(1-propinyl)-6'H-benzo[10,9,11]estra-4,15-dien-3-one;

E: 9,11α-dihydro-17α-ethinyl-17β-hydroxy-6'H-benzo [10,9,11]-18a-homoestr-4-en-3-one;

F: 9,11α-dihydro-17β-hydroxy-17α-(1-propinyl)-6'H-benzo[10,9,11]-18a-homoestr-4-en-3-one;

G: 9,11α-dihydro-17α-ethinyl-17β-hydroxy-6'H-benzo [10,9,11]-18a-homoestra-4,15-dien-3-one;

H: 9,11α-dihydro-17β-hydroxy-17α-(1-propinyl)-6'H-benzo[10,9,11]-18a-homoestra-4,15-dien-3-one;

I: 17-(acetyloxy)-9,11α-dihydro-6'H-benzo[10,9,11]-19-norpregn-4-ene-3,20-dione;

K: 17-(acetyloxy)-9,11α-dihydro-6'H-benzo[10,9,11]-19-norpregna-4,6-diene-3,20-dione;

L: 17-(acetyloxy)-9,11α-dihydro-β-methyl-6'H-benzo [10,9,11]-19-norpregna-4,6-diene-3,20-dione.

But while this strong bond in the known compounds leads first of all to pronounced competitive progesterone-antagonistic activity, and these compounds can thus primarily be used to induce abortions, against hormonal irregularities, to induce menstruation and to induce labor, the compounds according to the invention are surprisingly distinguished by greatly agonistic, i.e., progestogenic activity.

The progestogenic action was determined in the known pregnancy maintenance test in the rat after subcutaneous administration of the compounds. The results are compiled in Table 2:

TABLE 2

Pregnancy Maintenance Test on the Rat after S.C. Administration

| Compound | Fully effective at [mg/day/animal] |
| --- | --- |
| A | 0.1 |
| B | 0.1 |
| C | 0.03 |
| D | 0.03 |
| E | 0.03 |
| F | 0.1 |
| G | 0.03 |
| H | 0.1 |
| I | 0.1 |
| J | 0.1 |

TABLE 2-continued

Pregnancy Maintenance Test on the Rat after S.C. Administration

| Compound | Fully effective at [mg/day/animal] |
|---|---|
| K | 0.1 |

The compounds of general formula I according to the invention thus have at their disposal very strong progestogenic effectiveness with only weak androgenic or even weak antiandrogenic activity (dissociation).

Because of their progestogenic activity, the new compounds of general formula I can be used alone or in combination with estrogens in preparations for contraception.

The dosage of the compounds according to the invention in contraception preparations should be preferably 0.01 to 2 mg per day.

The progestogenic and estrogenic effective components are preferably orally administered together in contraception preparations. The daily dose is preferably administered once.

As estrogens, preferably synthetic estrogens, such as ethinylestradiol,14α,17α-ethano-1,3,5(10)-estratriene-3, 17β-diol (WO 88/01275) or 14α,17α-ethano-1,3,5(10)-estratriene-3,16α,17β-triol (WO 91/08219) are suitable.

The estrogen is administered in an amount which corresponds to that of 0.01 to 0.05 mg of ethinylestradiol.

The new compounds of general formula I can also be used in preparations for treating gynecological disorders and for substitution therapy. Because of their advantageous action profile, the compounds according to the invention are especially well-suited to treat premenstrual symptoms, such as headaches, depressive psychoses, water retention and mastodynia. The daily dose in the treatment of premenstrual symptoms is approximately 1 to 20 mg.

The formulation of the pharmaceutical preparations based on the new compounds takes place in a way known in the art, by the active ingredient, optionally in combination with an estrogen, being processed with the vehicles usual in galenicals, diluents, optionally flavoring substances, etc., and converted to the desired form of administration.

For the preferred oral administration, especially tablets, coated tablets, capsules, pills, suspensions or solutions are suitable.

For parenteral administration, especially oily solutions, such as, for example, solutions in sesame oil, castor oil and cottonseed oil, are suitable. To increase the solubility, solubilizers, such as, for example, benzyl benzoate or benzyl alcohol, are added.

It is also possible to incorporate the substances according to the invention in a transdermal system and thus to administer them transdermally.

Finally, the new compounds can also be used as progestogenic component in the compositions that have recently become known for female birth control, which are distinguished by the additional use of a competitive progesterone antagonist (H. B. Croxatto and A. M. Salvatierra in Female Contraception and Male Fertility Regulation, ed. by Runnebaum, Rabe & Kiesel—Vol. 2, Advances in Gynecological and Obstetric Research Series, Parthenon Publishing Group—1991, page 245).

The dosage lies in the already indicated range, the formulation can take place as in conventional OC preparations. The administration of additional, competitive progesterone antagonists can in this case also be performed sequentially.

The new compounds of general formula I are produced according to the invention by a compound of general formula II

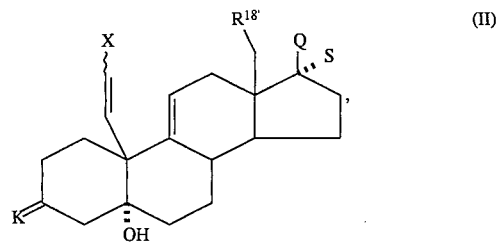

in which

K stands for a keto protecting group or a protected hydroxy group and a hydrogen atom, X stands for a chlorine or bromine atom in syn position or anti-position, $R^{18}$ stands for a hydrogen atom or a methyl group and Q stands for a hydroxy group in β-position and S stands for a hydrogen atom in α-position or Q and S together stand for a keto-oxygen atom of furthermore, Q and S stand for one of the $R^{17\beta}/R^{17\alpha}$ substituent combinations mentioned in formula I including the spiro compounds, and hydroxy groups and/or keto groups present in them are optionally protected, a) being converted by radical cyclization to a compound of general formula III

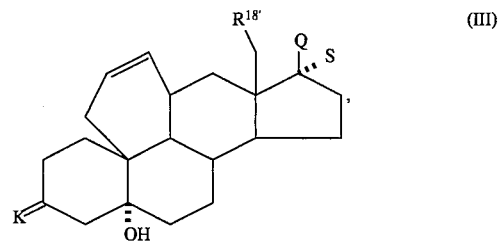

in which $K^{18}$ as well as Q and S have the meaning indicated in formula II, b) then, if Q stands for a hydroxy group, the latter optionally being oxidized, c) if $R^{11}$ $R^{11'}$, and $R^{19}$ ultimately are to be hydrogen atoms, the 19,11β-etheno bridge being hydrogenated, or d) if $R^{19}$ ultimately is to stand for a hydrogen atom and $R^{11}$ and $R^{11'}$ together for an additional double bond, the double bond in the 19,11β-etheno bridge being isomerized in 11-position (exo position), e) optionally a 15,16-double bond being introduced in the D-ring and the latter f) optionally being isomerized in 14,15-position or g) by methylenation in the corresponding 15β,16β-methylene compound as well as h) if Q and S together mean a keto-oxygen atom, being synthesized by nucleophilic addition of substituent $R^{17\alpha}$ or a reactive precursor of $R^{17\alpha}$ and optionally etherification or esterification of the 17β-hydroxy group with a reagent yielding corresponding radical $R^{21}$ or the 17α-hydroxy-17β-alkanoyl substitution pattern and the 17α-hydroxy group optionally being etherified or esterified with a reagent yielding corresponding radical $R^{23}$, i) optionally by partial or complete hydrogenation of an unsaturated $C_{17}$ side chain and j) optionally by oxidation of the corresponding 17-(3-hydroxypropyl) or 17-(4-hydroxybutyl) compound to form the 17-spirolactone or k) optionally by ring closure reaction of the corresponding (Z)-17α-(3-hydroxyprop-1-enyl) or (Z)-17α-(4-hydroxybut-1-enyl)-17β-hydroxy compound or the corresponding compounds saturated in the side chain to form the spiroether and l) by acid treatment in a water-miscible solvent in the $\Delta^4$-3-keto system, and other present protecting groups also being cleaved, and thus being converted to a compound of general formula I, and this compound of general formula I optionally m) by introduction of a 1,2- and/or 6,7-double bond and optionally methylenation of one or two double bond(s), n) by introduction of a straight-chain or branched-chain alkyl radical in α- or β-position or a thio group —$SR^{20}$ in 7-position, o) by epoxidation of the 6,7-double bond and opening the epoxide with hydrogen halide (Hal=F, Cl, Br, I) and elimination of the formed 7α-hydroxy group, p) by 6α-hydroxymethylation and subsequent dehydration to the 6-methylene compound, q) by isomerization of the double bond of the 6-methylene group in exo position or by direct introduction of a 6-alkyl group (6-alkyl-4,6-dien-3-one), r) being converted by hydrogenation of the 6-methylene group to a compound of general formula I in which $R^1$, $R^2$, $R^{14}$, $R^{15}$, $R^{16}$, $R^{17\alpha}$, $R^{17\beta}$, $R^{18}$, $R^{11}$ and $R^{19}$ have the meaning ultimately desired, and $R^{6a}$ is an α-methyl group and $R^{6b}$ and $R^7$ each represent a hydrogen atom or together an additional bond, or s) if $R^{6a}$ ultimately is to be a straight-chain or branched-chain, saturated alkyl radical, in α- or β-position, with up to 4 carbon atoms, being converted by ketalization with simultaneous isomerization of the 4(5)-double bond after 5(6), epoxidation of the 5(6)-double bond and nucleophilic opening of the 5,6α-epoxide with protected 3-keto group with a straight-chain or branched-chain, saturated alkylmagnesium halide or alkyllithium compound with up to 4 carbon atoms in the alkyl radical and cleavage of the 3-keto protecting group in the formed 5α-hydroxy-6β-alkyl compound under mild acid conditions to the corresponding 3-keto-5α-hydroxy-6β-alkyl compound and basic elimination of the 5α-hydroxy group in the corresponding 3-keto-4-ene compound of general formula I with 6-alkyl group in β-position or by cleavage of the 3-keto protecting group under more drastic conditions in the corresponding 3-keto-4-ene compound of general formula I with 6-alkyl group in α-position and t) optionally one of the above obtained 3-keto compounds with hydroxylamine hydrochloride in the presence of tertiary amines at a temperature between −20° and +40° C. in the 3-hydroxyimino compound (W=>N~OH:~means OH in syn or anti-position) or u) optionally in the 3-thioketal, preferably the 3-(1',3'-ethylenedithio)-ketal, being converted, and the latter being cleaved reductively to the compound of general formula I, in which W stands for two hydrogen atoms.

The synthesis route for the compounds containing the novel bridging is shown in diagram 1:

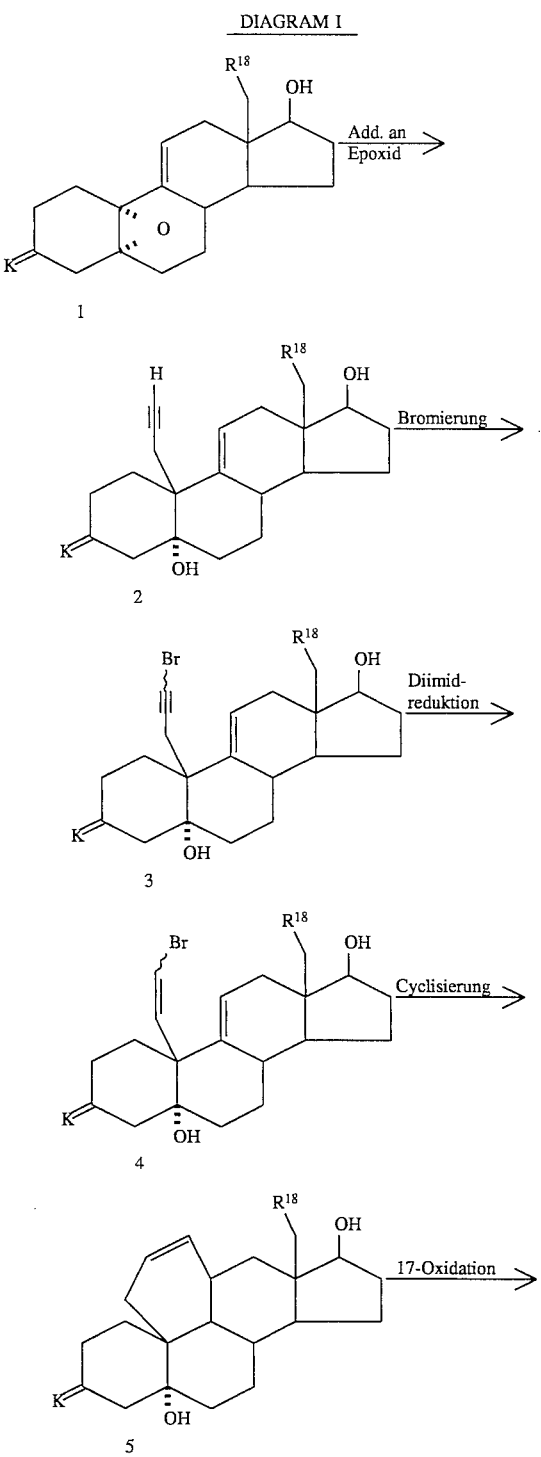

DIAGRAM I

-continued
DIAGRAM I

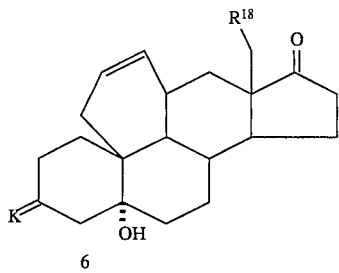

6

[KEY:]
Add. an Epoxid=addition to epoxide
Bromierung=bromation
Diimid reduktion=diimide reduction
Cyclisierung=cyclization
Oxidation=oxidizing agent According to diagram 1, epoxide 1 described, e.g., in European Patent Applications 0110434 and 0127864, in which $R^{18}$ stands for a hydrogen atom or a methyl group and K stands for a ketal protecting group, is converted to a compound of formula 2 by opening with propargylmagnesium halides (for illustration, see "Synthesis of Acetylenes, Allenes and Cumulenes," L. Brandsma and H. D. Verkruijsse, p. 16, Elsevier Scientific Publishing Company, Amsterdam, Oxford, New York (1981)). K is a standard ketal protecting group, for example, the ethylenedioxy- or the 2,2-dimethylpropylene-1,3-dioxy group. Also, other standard keto protecting groups are suitable. K can also mean a protected hydroxy group and a hydrogen atom, and the hydroxy group is then protected, for example, as methoxymethyl-, methoxyethyl-, tetrahydroxypyranyl- or silyl ether. The keto group is achieved by cleavage of the protecting group and oxidation of the free hydroxy group.

Compound 2 is then bromated according to a known process at the terminal end of the triple bond (H. Hofmeister, K. Annen, H. Laurent and R. Wiechert, Angew. Chem. [Applied Chem.] 96, p. 720 (1984)). Then, obtained compound 3 is converted by hydrogenation or hydride-transfer to vinyl halide 4. Preferably, the reaction is performed by diimide reduction.

The radical cyclization of compound 4 takes place analogously to the cyclization of corresponding aryl halogenations already described several times (see, e.g., E. Ottow, G. Neef and R. Wiechert; Angw. Chem. 101, p. 776 (1989)). Of the possible processes to generate the intermediate radicals, especially two are also used here:

The reaction with trialkyl stannanes, preferably with tributyltin hydride, in suitable solvents, such as, e.g., toluene, or the reaction with lithium in liquid ammonia, mixed with an organic solvent, such as, e.g., tetrahydrofuran at temperatures between −78° and −33° C.

Compound 5 can then be converted in a known way by oxidation of the 17-hydroxy function to 6. Compounds 5 and 6 are initial products in the production of compounds of general formula I.

If $R^{11}$, $R^{11'}$ $R^{19}$ are each a hydrogen atom, the double bond present in 5 or 6 can be hydrogenated according to known processes.

If $R^{19}$ is to be a hydrogen atom and $R^{11}$ and $R^{11'}$ together stand for an additional double bond, the isomerization of the original double bond ($R^{11}$=H, $R^{11'}$ and $R^{19}$ form together an additional bond) is achieved by heating compound 5 or 6 in ethanol with 5%-palladium-carbon catalyst, which was pre- treated either with hydrogen or by heating with a small amount of cyclohexene. But the isomerization can also be achieved by reaction with palladium-carbon catalyst in, e.g., ethanol or tetrahydrofuran/ethanol mixtures under an atmosphere of hydrogen pressure at room temperature or by boiling this reaction mixture with cyclohexene instead of hydrogen.

The next steps comprise then optionally desired functionalizations in the D-ring: the introduction of a 15,16-double bond ($R^{15}$ and $R^{16}$ form a common additional bond) takes place, e.g., by a modified Saegusa oxidation (I. Minami, K. Takahashi, I. Shimizu, T. Kimura, J. Tsuji; Tetrahedron 42 (1986) p. 2971; EP-A 0299913) of the corresponding enol compounds of the 17-ketone.

Optionally, the double bond can be isomerized after 14-position. For this purpose, the 15,16-ene compounds are treated with silica gel/triethylamine (S. Scholz et al., Lieb. Ann. Chem. 1989, p. 151).

For examples in which $R^{15}$ and $R^{16}$ together represent a methylene group in β-position, the introduction of this group takes place, e.g., by reaction of the corresponding 15,16-en-17-one compound with dimethyl sulfoxonium methylide (see, e.g., German laid-open specification 11 83 500, German laid-open specification 29 22 500, EP-A 0-0 19690, U.S. Pat. No. 4,291,029 A, E. J. Corey, M. Chaykovsky, J. Am. Chem. Soc. 84, p. 867 (1962)).

After D-ring modification has been completed, the additional steps are aimed first at the introduction of radicals $R^{17\alpha}$ and $R^{17\beta}$ to the C-17 atom. This introduction takes place analogously to processes known in the literature (e.g., J. Fried, J. A. Edwards, "Organic Reactions in Steroid Chemistry," von Nostrand Reinhold Company, 1972, Vol. 1 and 2; "Terpenoids and Steroids," Specialist Periodical Report, The Chemical Society, London, Vol. 1–2) in most cases by nucleophilic addition of substituent $R^{17\alpha}$ or a reactive precursor of $R^{17\alpha}$ to the C-17 atom.

In the case of an easily enolizable 17-ketone, such as, e.g., the 14,15-ene compounds, nucleophiles are introduced while adding cerium salts (T. Imamoto, N. Takiyana, K. Nakamura, Y. Sugiura, Tet. Lett. 25, 4233 (1984)).

The introduction of substituent C≡C-B as $R^{17\alpha}$ with the above-mentioned meanings for B takes place with the help of metalated compounds, which also can be formed in situ and brought to reaction with the 17-ketone. The formation of the metalated compounds takes place, for example, by reaction of the acetylenes with alkali metals, especially potassium, sodium or lithium, in the presence of an alcohol or in the presence of ammonia. But the alkali metal can also be effective in the form of, e.g., methyllithium or butyllithium. Compounds in which B=bromine or iodine are produced in a known way from the 17-ethinyl compounds (see, e.g., H. Hofmeister, K. Annen, H. Laurent and R. Wiechert, Angew. Chem. 96, 720 (1984)).

The introduction of 3-hydroxy-1-propine in 17-position takes place by reaction of the 17-ketone with the dianion of propargyl alcohol (3-hydroxypropine), e.g., the dipotassium salt of the propargyl alcohol generated in situ or with corresponding derivatives protected in the hydroxy function, such as, e.g., the lithium compound of 3-[(tetrahydro-2H-pyran-2-yl)oxy]-1-propine.

The hydroxypropyl and hydroxypropenyl compounds can be produced from the hydroxypropinyl derivatives. The production of the hydroxypropyl chain takes place, e.g., by hydrogenation at room temperature and normal pressure in solvents such as methanol, ethanol, tetrahydrofuran or ethyl acetate while adding noble metal catalysts such as platinum or palladium.

The production of compounds with a Z-configured double bond in the side chain takes place by hydrogenation of the acetylenic triple bond with a deactivated noble metal catalyst, e.g., 10% palladium on barium sulfate in the presence of an amine or 5% palladium on calcium carbonate while adding lead(II) acetate. The hydrogenation is terminated after the absorption of an equivalent of hydrogen.

Compounds with an E-configured double bond in the side chain result by reduction of the triple bond, e.g., with sodium in liquid ammonia (K. N. Cambell, L. T. Eby, J. Am. Chem. Soc. 63 (1941), p. 216), with sodium amide in liquid ammonia or with lithium in low-molecular amines (R. A. Benkeser et al., J. Am. Chem. Soc. 77 (1955), p. 3378).

The introduction of the hydroxyalkenes and hydroxyalkanes can also take place directly by reaction of the 17-ketone with metalated derivatives (E. J. Corey, R. H. Wollenberg, J. Org. Chem. 40, 2265 (1975); H. P. On. W. Lewis, G. Zweifel, Synthesis 1981, p. 999; G. Gohiez, A. Alexakis, J. F. Normant, Tet. Lett. 1978, p. 3013; P. E. Eaton et al., J. Org. Chem. 37, 1947). The introduction of homologous hydroxyalkine, hydroxyalkene and hydroxyalkane groups is possible in a corresponding way.

Products in which $R^{17\alpha}/R^{17\beta}$ stands for

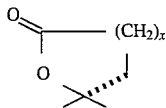

with x=1 or 2, can be produced from the 17-(3-hydroxypropyl) or 17-(4-hydroxybutyl) compounds by oxidation in a known way, e.g., with Jones reagent, manganese dioxide, pyridinium dichromate, pyridinium chlorochromate, chromic acid pyridine or Fetizon reagent.

Products in which $R^{17\alpha}/R^{17\beta}$ stands for

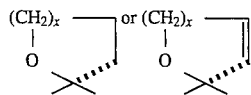

with x=1 or 2, can be produced by ring closure reaction of the corresponding (Z)-17α-(3-hydroxyprop-1-enyl) or (Z)-17α-(4-hydroxy-1-butenyl)-17β-hydroxy compounds or the compounds suitably saturated in the side chain. Compounds with a saturated spiro ether can be produced by hydrogenation of the unsaturated spiro ether on platinum or palladium catalysts.

17α-1,2-Alkdienyl-substituted steroids are, for example, accessible by reaction of the 17α-(3-hydroxy-1-alkine)-substituted compounds optionally protected as tetrahydropyranyl ether, α-alkoxyethyl ether, alkyl or aryl sulfonates with complex hydrides in aliphatic or alicyclic ethers (see, e.g., A. Burger, J.-P. Roussel, C. Hetru, J. A. Hoffmann and B. Luu, Tetrahedron 45, 155 (1989); A. Claesson, L.-I. Olsson and C. Bogentoft, Acta Chem. Scand. 27, 2941 (1973); L. -I. Olsson and A. Claesson, Acta Chem. Scand. B31, 614 (1977)) but also according to other processes known in the literature (see, e.g., DE-AS 19 58 5333; DE-OS 16 68 679).

The introduction of a trifluoromethyl group is possible by reaction of the 17-ketone with trifluoromethyltrimethylsilane in the presence of tetrabutylammonium fluoride (see R. Krshnamurti, D. R. Bellew and G. K. S. Prahash, J. Org. Chem., 56, 984 (1991).

The synthesis of the 17-cyanomethyl side chain takes place from the 17-ketone either directly by addition of acetonitrile or by cleavage of the spiro epoxide with HCN according to K. Ponsold et al., Z. Chem. 18, (1978) 259–260.

The synthesis of 16,17α-methylene-17β-alkanoyl-substituted compounds takes place according to processes known in the literature. Thus, $\Delta^{16}$-17-perfluorosulfonyloxy compounds can be produced, for example, starting from the 17-ketones, which can be coupled in the presence of transition metal catalysts with alkoxyvinyltin or zinc compounds (see, e.g., M. Kosugi, T. Sumiya, Y. Obara, M. Suzuki, H. Sano and T. Migita, Bull. Chem. Soc. Jpn. 60, 767 (1987); P. G. Ciattini, E. Morera and G. Ortar, Tetrahedron Lett. 31, 1889 (1990)). Acid hydrolysis of the coupling products produces the $\Delta^{16}$-17-acetyl compounds. These enones can be reacted according to the processes indicated above for the cyclopropanation of $\Delta^{15}$-17-ketones with trimethylsulfoxonium iodide to 16,17α-methylene-17βa-acetyl compounds, or else converted by conjugated addition of alkyl copper compounds to the 16α-alkyl-progesterone derivatives.

Compounds, in which $R^{17\alpha}$ is an alkyl radical and $R^{17\beta}$ is an alkanoyl radical, can be produced, for example, from $\Delta^{16}$-17-alkanoyl compounds or 17α-hydroxy-17β-alkanoyl compounds, by 17-enolate anions being produced by reduction with lithium in liquid ammonia mixed with tetrahydrofuran, which can be alkylated with alkyl halides to the desired compounds (see, e.g., M. J. Weiss, R. E. Schaub, G. R. Allen, Jr., J. F. Poletto, C. Pidacks, R. B. Conrow and C. J. Coscia, Tetrahedron 20, 357 (1964).

The production of derivatives, in which $R^{17\alpha}$ and $R^{17\beta}$ together stand for

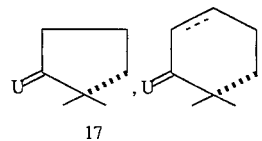

takes place starting from 17-ketone according to methods known in the literature (e.g., EP-A-O 444 3951, 1991; and EP-A-0 154 429; 1989). In this connection, the corresponding 17α-(2-propenyl) compounds (allylation with allyl bromide) are produced, for example, by reductive allylation of the above-mentioned $\Delta^{16}$-17-acetyl compound. The terminal double bond is then converted either by hydroboration, e.g., with 9.BBN (9-borabicyclononane), oxidative working up and further oxidation to the corresponding $C_3$-aldehyde or else by ozonolytic decomposition to the $C_2$-aldehyde. The 6-ring or 5-ring spiro ketones can then be produced via aldol reaction. In this case, first the α,β-unsaturated ketones result, which optionally can be reduced according to known methods to the saturated ketones.

The introduction of a hydroxy progesterone substitution pattern (17β=acetyl, 17α=hydroxy) or the synthesis of corresponding homologous 17α-hydroxy-17β-alkanoyl compounds takes place according to processes known in the literature. In this connection, the method by a 17β-cyano-17α-hydroxy compound (cyanohydrin method; see, i.a., DE 39 31 064 A1 (1989); GDR Patent 147 669 (1981); DE 21 10 140 (1971); Jap. Patent 57062296-300 (1982); J. C. Gase and L. Nedelec, Tet. Lett. 1971, p. 2005; J. N. M. Batist, N. C. M. E. Barendse, A. F. Marx, Steroids 1990, p. 109) is especially to be emphasized.

In this case, the 17-ketone is reacted by reaction with, for example, acetone cyanohydrin (2-hydroxy-2-methylpropanenitrile) in suitable solvent systems, e.g., ethanol or methanol and dichloromethane at a suitable (in most cases slightly basic) pH (is adjusted by addition of KCN or NaCN and KOH or NaOH, respectively). Under these reaction conditions, a crystallizing out of the 17β-cyano compound can be achieved. The 17α-hydroxy function is then protected and then the cyano group can be reacted with $C_1$-$C_4$ alkyllithium, e.g., with methyllithium or $C_1$-$C_4$ alkylmagnesium halides, e.g., methylmagnesium halides, to then achieve a 17α-hydroxy-17β-alkanoyl compound after acid cleavage. Starting from the 17α-hydroxy-17β-alkanoyl compounds, the 17α-alkanoyloxy derivatives can then be obtained in a known way.

Also, the conversion of 17α-ethinyl-17β-nitrooxy compounds (see H. Hofmeister, K. Annen, H. Laurent and R. Wiechert, Chem. Ber. 111,3086 (1978)) or of allenesulfoxides generated from 17α-ethinyl-17β-hydroxy compounds by reaction with phenylsulfenyl chloride (see V. Van-Rheenen and K. P. Shephard, J. Org. Chem. 44, 1582 (1979)) to the 17α-hydroxy-17β-acetyl compounds should be especially emphasized.

17β-Acetyl-17α-fluorine compounds can be produced, e.g., from the corresponding 17β-acetyl-17α-hydroxy compounds by reaction with DAST (diethylaminosulfur trifluoride) in suitable solvents, such as, for example, trichloromethane.

The subsequent release of the 3-keto function under dehydration and forming the 4(5)-double bond takes place by treatment with acid or an acid ion exchanger. The acid treatment takes place in a way known in the art, by the corresponding 5α-hydroxy-3-ketal being dissolved in a water-miscible solvent, such as aqueous methanol, ethanol or acetone, and catalytic amounts of mineral or sulfonic acid, such as hydrochloric acid, sulfuric acid, phosphoric acid, perchloric acid or p-toluenesulfonic acid, or an organic acid, such as ethyl acetate, being allowed to act on the solution until existing protecting groups are removed. The reaction, which occurs at temperatures of 0° to 100° C., can also be performed with an acid ion exchanger. The course of the reaction can be tracked with analytical methods, for example, samples gathered by thin-layer chromatography.

The next steps normally are aimed at the synthesis of radicals $R^{6a}$, $R^{6b}$, $R^7$ $R^1$, $R^2$.

For end compounds in which a 1,2- and a 6,7-double bond exists or for corresponding intermediate products in which two double bonds beside one another are desired, the introduction of two double bonds can simultaneously take place starting from 3-ketone (W=oxygen), mainly by a 2,6-dibromation and subsequent elimination (see, e.g., German laid-open specification 11 19 266). But often it is necessary to introduce the two double bonds in succession because of the other functionalities in the molecule. In this case, first the introduction of a 6,7-double bond normally occurs. This introduction is possible by a dienol ether bromation and subsequent hydrobromic acid cleavage (see, e.g., J. Fried, J. A. Edwards, Organic Reactions in Steroid Chemistry, von Nostrand Reinhold Company 1972, pp. 265–374).

The dienol ether bromation, e.g., can take place analogously to the instructions in Steroids 1, 233. The hydrobromic acid cleavage is possible by heating the 6-bromine compound with basic agents, such as, e.g., LiBr or $LiCO_3$ in aprotic solvents, such as dimethylformamide at temperatures of 50°–120° C. or else by the 6-bromine compounds being heated in collidine or lutidine.

The introduction of a 1,2-double bond can take place, depending on the desired end compound, directly after introduction of the 6,7-double bond or else in a later intermediate stage. This dehydrogenation is possible preferably chemically or microbiologically according to processes known in the literature (e.g., DE 34 02 329 A1 and EP-A-0 150 157).

The chemical dehydrogenation takes place, for example, by heating with selenium dioxide, 2,3-dichloro-5,6-dicyanobenzoquinone, chloranil, thallium triacetate or lead tetraacetate in suitable solvents, such as, e.g., dioxan, tert-butanol, tetrahydrofuran, toluene, benzene or mixtures of these solvents.

But the introduction of the 1,2-double bond can also take place by a modified Saegusa oxidation (I. Minami, K. Takahashi, I. Shimizu, T. Kimura, J. Tsuji, Tetrahedron 42 (1986), p. 2971; EP-A-0 299 913) of the corresponding enol compounds of the 3-ketone.

Compounds, which have a 1,2α-methylene function, are produced from the 1,2-unsaturated compounds by reaction with dimethylsulfoxonium methylide analogously to the production of the 15,16β-methylene compound (see above). In this case, a selective introduction of the 1,2-methylene function is also possible in the presence of the 4,6-dien-3-one unit (see, e.g., German laid-open specification 11 83 500).

For compounds with a 6,7-methylene function, the introduction also takes place from the dienone by reaction with dimethylsulfoxonium methylide, but here a mixture of the α- and β-isomers occurs (the ratio is a function of the substrates used and is approximately 1:1), which can be separated, e.g., by column chromatography.

Compounds with $R^7$ equal to alkyl or $SR^{20}$, in which $R^{20}$ has the above-mentioned meanings, are produced from the 4,6-dien-3-one compounds by 1,6-addition according to known methods (J. Fried, J. A. Edwards: "Organic Reactions in Steroid Chemistry," von Nostrand Reinhold Company 1972, pages 75 to 82; and A. Hosomi, H. Sakurai, J. Am. Chem. Soc. 99 (1977), p. 1673).

The introduction of the 7-alkyl functions takes place in this case generally by the dialkyl copper lithium compounds. The introduction of an $SR^{20}$ group takes place by 1,6-addition of thioacetic acid. In this case, usually mixtures of the stereoisomers result, and an influencing of this reaction in the case of the thioacetic acid addition by adding Lewis acids, such as, e.g., boron trifluoroetherate in tetrahydrofuran as solvent, results in a drastic increase of the 7α-isomers.

Compounds, in which $R^{6a}$ represents a chlorine atom and $R^{6b}$ and $R^7$ together form an additional bond, are also produced starting from the 4,6-dien-3-one compounds. In this connection, first the 6,7-double bond is epoxidated by using organic peracids, such as, e.g., meta-chloroperbenzoic acid in methylene chloride, optionally in the presence of sodium bicarbonate solution (see W. Adam et al., J. Org. Chem. 38 (1973), p. 2269). The opening of this epoxide and the elimination of the primarily formed 7α-hydroxy group takes place, e.g., by reaction with hydrogen chloride gas in glacial acetic acid (see, i.a., DE-A-11 58 966 and DE-A 40 06 165). But the two reactions can also be performed in succession, by the epoxide first being nucleophilically opened with, e.g., alkali metal halides (e.g., LiCl) in solvents such as acetic acid and the formed 7α-hydroxy group then being eliminated after conversion to a leaving group (e.g., the mesylate or tosylate).

The introduction of a β-methylene group can take place, e.g., starting from a 3-amino-3,5-diene derivative by reaction with formalin in alcoholic solution with formation of a 6α-hydroxymethyl group and subsequent acid dehydration, e.g., with hydrochloric acid in dioxan/water. But the dehydration can also take place in a way that first a leaving group is introduced and then eliminated. As leaving groups, e.g., the mesylate, tosylate or benzoate are suitable (see DE-A-34 02 329 A1; EP-A-0 150 157; U.S. Pat. No. 4,584,288 (86); K. Nickisch et al., J. Med. Chem. 34, 2464 (1991)).

Another possibility for introducing the 6-methylene compounds consists in the direct reaction of the 4(5)-unsaturated 3-ketones with acetals of formaldehyde in the presence of sodium acetate with, e.g., phosphorus oxychloride or phosphorus pentachloride in suitable solvents such as chloroform (see, e.g., K. Annen, H. Hofmeister, H. Laurent and R. Wiechert, Synthesis 1982, p. 34).

The 6-methylene compounds can be used to produce compounds of general formula I, in which $R^{6a}$ is equal to methyl and $R^{6b}$ and $R^7$ form a common additional bond.

In this connection, e.g., a process described by D. Burn et al. in Tetrahedron 21 (1965), p. 1619, can be used, in which an isomerization of the double bond is achieved by heating the 6-methylene compounds in ethanol with 5% palladium-carbon catalyst, which was pretreated either with hydrogen or by heating with a small amount of cyclohexene. The isomerization can also take place with a non-pretreated catalyst, if a small amount of cyclohexene is added to the reaction mixture.

The occurrence of small portions of hydrogenated products can be prevented by adding an excess of sodium acetate.

But the production of 6-methyl-4,6-dien-3-one derivatives can also take place directly (see K. Annen, H. Hofmeister, H. Laurent and R. Wiechert, Lieb. Ann. 1983, p. 712).

Compounds in which $R^{6a}$ represents an s-methyl function can be produced from the 6-methylene compounds by hydrogenation under suitable conditions. The best results (selective hydrogenation of the exo-methylene function) are achieved by transfer hydrogenation (E. A. Brande, R. P. Linstead and P. W. D. Mitchell, J. Chem. Soc. 3578 (1954). If the 6-methylene derivatives are heated in a suitable solvent, such as, e.g., ethanol, in the presence of a hydrogen donor, such as, e.g., cyclohexene, 6α-methyl derivatives can be achieved in very good yields. Small portions of 6β-methyl compounds can be acid-isomerized (see, e.g., D. Burn, D. N. Kirk and V. Petrow, Tetrahedron, (1965), p. 1619).

Also, targeted production of 6β-alkyl compounds is possible. In this connection, the 4(5)-unsaturated 3-ketones are reacted, e.g., with ethylene glycol, trimethyl orthoformate in dichloromethane in the presence of catalytic amounts of an acid (e.g., p-toluenesulfonic acid) to the corresponding 3 ketals. During this ketalization, the double bond isomerizes in 5(6)-position. A selective epoxidation of this 5(6)-double bond is possible, e.g., by using organic peracids in suitable solvents such as, e.g., dichloromethane. As an alternative to this, the epoxidation can also take place with hydrogen peroxide in the presence of, e.g., hexachloroacetone or 3-nitrotrifluoroacetophenone. The formed 5,6α-epoxides can then be axially opened by using, e.g., alkylmagnesium halides or alkyllithium compounds. 5α-Hydroxy-6β-alkyl compounds are thus obtained. The cleavage of the 3-keto protecting group can take place while obtaining the 5α-hydroxy function by treatment under mildly acid conditions (acetic acid or 4 n hydrochloric acid at 0° C.). Basic elimination of the 5α-hydroxy function with, e.g., diluted aqueous sodium hydroxide solution produces the 3-keto-4-ene compounds with a 6-alkyl group in β-position. As an alternative to this, the ketal cleavage produces the corresponding 6α-alkyl compounds under more drastic conditions (aqueous hydrochloric acid or another strong acid).

The obtained compounds of general formula I with W meaning an oxygen atom can optionally be converted by reaction with hydroxylamine hydrochloride in the presence of tert-amines at temperatures between –20° and +40° C. to the oximes (general formula I with X meaning N~OH, in which the hydroxy group can be in syn or anti-position).

The removal of the 3-oxo group in an end product of general formula I with W meaning two hydrogen atoms can take place, for example, according to the instructions indicated in DE-A 28 05 490 by reductive cleavage of the thioketal.

Also to the object of this invention belong the intermediate compounds of general formula III'

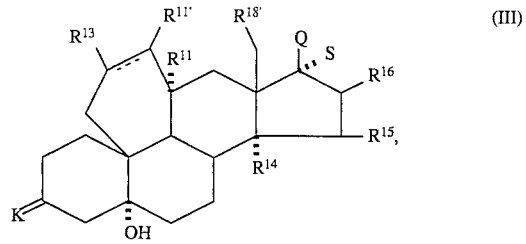

in which

K stands for a keto protecting group or a protected hydroxy group and a hydrogen atom, $R^{11'}$ and $R^{19}$ together stand for an additional bond and $R^{11}$ stands for a hydrogen atom in α-position or $R^{19}$ stands for a hydrogen atom and $R^{11}$ and $R^{11'}$ together stand for an additional bond or $R^{11}$ $R^{11'}$ $R^{19}$ and each stand for a hydrogen atom, $R^{14}$,$R^{15}$ and $R^{16}$ and stand for the substituents indicated in this connection in formula I, $R^{18}$ stands for a hydrogen atom or a methyl group and Q stands for a hydroxy group in β-position and S stands for a hydrogen atom in α-position or Q and S together stand for a keto-oxygen atom or furthermore Q and S stand for one of the $R^{17\beta}/R^{17\alpha}$ substituent combination mentioned in formula I including the spiro compounds, in which hydroxy and/or keto groups present therein are optionally protected.

These compounds have already passed through the cyclization reaction and can still exhibit in 17-position the original hydroxy group, already the keto group or the final $R^{17\alpha}/R^{17\beta}$ substituent pattern.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patent and publications, cited above and below, and of corresponding German Application No. P 42 35 220.7 of Oct. 13, 1992, are hereby incorporated by reference.

The following examples are used for a more detailed explanation of this invention:

EXAMPLES

General Comments:

I) All tests are performed under protective gas atmosphere (argon)

II) If nothing else is indicated, the working up of the experiments takes place as follows:

The reaction solution is poured either on saturated aqueous sodium chloride solution (A), saturated aqueous sodium bicarbonate solution (5) or saturated aqueous ammonium chloride solution (C). Then, it is extracted several times with ethyl acetate. The combined organic phases are washed either with saturated aqueous ammonium chloride solution (D) or saturated aqueous sodium bicarbonate solution (E) as well as with saturated aqueous sodium chloride solution (F) and dried on sodium sulfate. Then, it is filtered and concentrated by evaporation in a vacuum.

III) If nothing else is indicated, the crude products obtained are purified by column chromatography on silica gel with a mixture of hexane/ethyl acetate.

IV) General Instructions:

1) Cleavage of C-3-ketals optionally with elimination of a 5α-hydroxy group as well as cleavage of an optionally present tetrahydropyranyl protecting group in the 17α-side chain:

5 mmol of initial material and 5 ml of 4 n hydrochloric acid are dissolved in 60 ml of acetone. It is allowed to stir for one more hour at room temperature as well as 30 minutes at 40° C. Subsequent aqueous working up (A, E, F) and purification produces the corresponding 3-ketone.

2) Addition of an ethinyl, propinyl or 1-butinyl side chain to C-17:

100 ml of absolute tetrahydrofuran is saturated at 0° C. over 30 minutes with ethine or propine gas; 5 g of 1-butine in 100 ml of tetrahydrofuran is introduced for the addition of 1-butinyl side chain. Then, 31 ml of a 1.6 molar solution of n-butyllithium in hexane is added and allowed to stir for 30 more minutes at 0° C. Then, a solution of the corresponding initial material (5 mmol) in absolute tetrahydrofuran is added. It is allowed to stir for one more hour at 0° C. and then aqueously worked up (C, F).

3) Oxidation with chromium trioxide/pyridine:

30 mmol of chromium trioxide is added to 10 ml of pyridine in 80 ml of dichloromethane at 0° C. It is stirred for 30 more minutes at 0° C. and then 5 mmol of the initial material in 15 ml of dichloromethane is added at 0° C. Then, it is allowed to stir for one more hour at 0° C. Then, the reaction solution is decanted and the residue is washed three times with dichloromethane. The combined organic phases are washed twice with 5% aqueous sodium hydroxide solution and once with saturated aqueous sodium chloride solution and dried on sodium sulfate. Then, it is filtered and concentrated by evaporation in a vacuum.

4) Introduction of a 15(16) double bond from a saturated 17-ketone via silylenol ether formation and subsequent Saegusa oxidation a) Production of the silylenol ether:

Lithium diisopropylamide is produced from 15 mmol of diisopropylamine in 100 ml of absolute tetrahydrofuran and 9 ml of a 1.5 molar solution of n-butyllithium in hexane at −30° C. Then, a solution of 5 mmol of the respective 17-ketone in 50 ml of absolute tetrahydrofuran is added and allowed to stir for one more hour at −30° C. Then, 17 mmol of trimethylchlorosilane is added. Then, the reaction mixture is allowed to come to room temperature and stirred for one more hour. The corresponding silylenol ether is obtained by aqueous working up (B, D, F).

b) Introduction of the 15(16)-double bond:

5 mmol of the silylenol ether described under a) is dissolved in 60 ml of acetonitrile. 5.5 mmol of palladium(II) acetate is added and allowed to stir for 8 more hours at room temperature. Then, the reaction solution is filtered on Celite and concentrated by evaporation in a vacuum.

Example 1

9,11α-Dihydro-17β-hydroxy-17α-methyl-6'H-benzo[10,9,11]estr-4-en-3-one a) 3,3-[2,2-Dimethyl-1,3-propanediylbis(oxy)]-19-ethinyl-5α-androst-9(11)-ene-5,17β-diol 3 g of mercury(II) chloride is added to a suspension of 48.6 g of magnesium chips in 700 ml of absolute diethyl ether. It is stirred for 30 more minutes and then cooled to 0° C. Then, first 7.5 ml of 3-bromopropine is added. After the start of the reaction (temperature increase), it is cooled to −5° C. Then, another 67.5 ml of 3-bromopropine is instilled at a speed at which the inner temperature does not exceed 0° C. After completion of the addition, it is stirred for 30 more minutes at 0° C. and then a solution of 50 g of 3,3-[2,2-dimethyl]-1,3-propanediylbis(oxy)]-5,10α-epoxy-5α-estr-9(11)-en-17β-ol in 300 ml of absolute tetrahydrofuran is slowly instilled. It is allowed to stir for one more hour at 0° C. and then excess magnesium is decanted. Then, 500 ml of saturated aqueous ammonium chloride solution is carefully added and allowed to stir for one hour at room temperature (strong gas generation). Then, it is aqueously worked up (F). After recrystallization of the crude product from diisopropyl ether, 45.2 g of 1a) is obtained.

$^1$H-NMR (CDCl$_3$): δ=5.42 ppm m (1H,H-11); 4.40 s (1H,OH); 3.75 dd (J=14,7.5 Hz,1H,H-17); 3.40–3.60 m (4H,ketal); 1.93 t (J=1.5 Hz,1H,ethine); 0.99 s (3H,Me-ketal); 0.92 s(3H,Me-ketal); 0.76 s (3H,C-18)

b) 19-(Bromoethinyl)-3,3-[2,2-dimethyl-1,3-propanediylbis(oxy)]-5α-androst-9(11)-ene-5,17β-diol 45 g of the substance described under 1a) is dissolved in 750 ml of acetone. 1.85 g of silver nitrate and 23.3 g of N-bromosuccinimide are added. Then, it is stirred for 20 more minutes at room temperature. Aqueous working up (B, F) yields 52.5 g of 1b), which is used without purification in the next stage.

c) 19-(2-Bromoethenyl)-3,3-[2,2-dimethyl-1,3-propanediylbis(oxy)]-5α-androst-9(11)-ene-5,17β-diol 52.5 g of the substance described under 1b) is dissolved in 1000 ml of a mixture of tetrahydrofuran and water (1:1). 79 g of p-toluenesulfonic acid hydrazide and 52 g of sodium acetate are added. Then it is refluxed for 4 hours. Aqueous working up (B, F) as well as purification produces 36.9 g of 1c) as white foam.

$^1$H-NMR (CDCl$_3$): δ6.18 ppm m (1H,vinyl); 5.85 m (1H,vinyl); 5.43 m (1H,H-11); 4.40 s (1H,OH); 3.73 dd (J=14,7.5 Hz,1H,H-17); 3.48–3.58 m (4H,ketal); 1.00 s (3H,Me-ketal); 0.98 s (3H,Me-ketal); 0.70 s (3H,C-18)

d) 9,11α-Dihydro-3,3-[2,2-dimethyl-1,3-propanediylbis(oxy)]-6'H-benzo[10,9,11]-5α-estrane-5,17β-diol Production with Use of Tributyltin Hydride:

20 g of the substance described under 1c) is dissolved in 500 ml of absolute toluene. 12 ml of tributyltin hydride and 25 mg of azobisisobutyronitrile are added and refluxed for one hour with simultaneous irradiation with a UV lamp. After completion of the reaction, the reaction solution is concentrated by evaporation in a vacuum, and the residue is purified by recrystallization from diisopropyl ether. 9.1 g of 1d) is obtained as white crystals. By column chromatography of the mother liquor on silica gel with a mixture of hexane/ethyl acetate, another 3.84 g of 1d) is obtained as white foam.

$^1$H-NMR (CDCl$_3$): δ=5.50 ppm dbr (J=10 Hz,1H,Bridge); 5.47 m (1H,Bridge); 4.37 s (1H,OH); 3.50–3.62 m (5H,ketal and H-17); 2.47 m (1H,H-11); 0.99 s (3H,Me-ketal); 0.98 s (3H,Me-ketal); 0.80 s (3H,C-18)

Production under Birch Conditions:

3.5 g of lithium is slowly added to 400 ml of condensed ammonia at −78° C. After completion of the dissolution, a solution of 5 g of the substance described under 1c) is instilled in 600 ml of absolute tetrahydrofuran. After completion of the addition, it is stirred for 15 more minutes at −40° C. Then, the reaction solution is quenched by adding water. The ammonia is allowed to escape overnight and it is aqueously worked up (F). After purification, in addition to 1.9 g of 1d), 1.6 g of 3,3-[2,2-dimethyl-1,3-propanediylbis(oxy)]-19-ethenyl-5α-androst-9(11)-ene-5,17β-diol is obtained.

1e) 9,11α-Dihydro-3,3-[2,2-dimethyl-1,3-propanediylbis(oxy)]-5-hydroxy-6'H-benzo [10,9,11]-5α-estran-17-one 1. Production from 1d)

According to general instruction 3), 11.34 g of 1e) is obtained as white foam from 12.9 g of the substance described under 1d), 18,5 g of chromium trioxide and 62 ml of pyridine in 450 ml of dichloromethane.

2. Alternative Production of 1e)

1e1) 3,3-[2,2-Dimethyl-1,3-propanediylbis(oxy)]-19-ethinyl-5-hydroxy-5α-androst-9(11)-en-17-one According to general instruction 3, 5 g of the substance described under 1a) is reacted. 4.82 g of 1e1) is obtained as white foam.

$^1$H-NMR (CDCl$_3$): δ=5.43 ppm dbr (J=5.5 Hz, 1H, H-11); 4.40 s (1H,OH); 3.40–3.60 m (4H,ketal); 1.92 t (J=1.5 Hz,1H,ethine); 1.02 s (3H,C-18); 0.95 s (3H,Me-ketal); 0.91 s (3H,Me-ketal)

1e2) 19-(2-Bromoethinyl)-3,3-[2,2-dimethyl-1,3-propanediylbis(oxy)]-5-hydroxy-5α-androst-9(11)-en-17-one Analogously to 1b), 4.82 g of the substance described under 1e1) is reacted with 5.5 g of N-bromosuccinimide and 200 mg of silver nitrate in 100 ml of acetone. 5.7 g of 1e2) is obtained, which is used as crude product in the next stage.

1e3) 19-(2-Bromoethenyl)-3,3-[2,2-dimethyl-1,3-propanediylbis(oxy)]-5-hydroxy-5α-androst-9(11)-en-17-one Analogously to example 1c), 5.7 g of the substance described under 1e2) is reacted with 9 g of p-toluenesulfonic acid hydrazide and 6 g of sodium acetate in 100 ml of a mixture of tetrahydrofuran and water (1:1). After purification, 3 g of 1e3) is obtained as white foam.

$^1$H-NMR (CDCl$_3$): δ=6.19 m (1H,vinyl); 5.83 m (1H, vinyl); 5.33 dbr (J=5.5 Hz,1H,H-11); 4.40 s (1H,OH); 3.45–3.60 m (4H,ketal); 1.00 s (3H,C-18); 0.95 s (3H,Me-ketal); 0.82 s (3H, Me-ketal )

1e) 9,11α-Dihydro-3,3-[2,2-dimethyl-1,3-propanediylbis(oxy)]-5-hydroxy-6'H-benzo[10,9,11]-5α-estran-17-one Analogously to 1d), 3 g of the substance described under 1e3) is reacted with 3 ml of tributyltin hydride and 25 mg of azobisisobutyronitrile in 100 ml of absolute toluene. After purification, 2.39 g of 1e) is obtained as white foam.

$^1$H-NMR (CDCl$_3$): δ=5.57 ppm dbr (J=10 Hz, 1H, Bridge); 5.49 m (1H,Bridge); 4.40 s (1H,OH); 3.50–3.60 m (4H,ketal); 2.53 m (1H,H-11); 1.00 s (3H,Me-ketal); 0.98 s (3H,Me-ketal); 0.92 s (3H,C-18)

1f) 9,11α-Dihydro-3,3-[2,2-dimethyl-1,3-propanediylbis(oxy)]-17α-methyl-6'H-benzo [10,9,11]-5α-estrane-5,17β-diol A solution of 882 mg of the compound, produced under 1e), in 20 ml of absolute tetrahydrofuran, is added to 13 ml of a 1.6 molar solution of methyllithium in diethyl ether at 0° C. under argon. It is stirred for 2 more hours at 0° C. and then aqueously worked up (C, F). 845 mg of 1f) is obtained as white foam, which is used without purification in the next stage.

1g) 9,11α-Dihydro-17β-hydroxy-17α-methyl-6'H-benzo[10,9,11]estr-4-en-3-one

According to general instruction 1), 839 mg of 1f) is reacted with 4 n hydrochloric acid in acetone. After purification, 594 mg of 1 g) is obtained as white foam.

$^1$H-NMR (CDCl$_3$): δ5.81 ppm sbr (1H,H-4); 5.61 dbr (J=10 Hz,1H,Bridge); 5.50 m (1H,Bridge); 2.69 m (1H,H-11); 1.23 s (3H,methyl); 0.95 s (3H,C-19)

Example 2

9,11α-Dihydro-17α-ethinyl-17β-hydroxy-6'H-benzo[10,9,11]estr-4-en-3-one a) 9,11α-Dihydro-3,3-[2,2-dimethyl-1,3-propanediylbis(oxy)]-17α-ethinyl-6'H-benzo[10,9,11]-5α-estrane-5,17β-diol According to general instruction 2), 1.24 g of the substance described under 1e) and 18.9 ml of a 1.6 molar solution of n-butyllithium in hexane as well as ethine gas in absolute tetrahydrofuran are reacted. After purification, 1.20 g of 2a) is obtained as white foam.

$^1$H-NMR (CDCl$_3$): δ5.55 ppm dbr (J=10 Hz,1H,Bridge); 5.48 m (1H,Bridge); 4.40 s (1H,OH); 3.50–3.62 m (4H, ketal); 2.59 s (1H,ethine); 2.52 m (1H,H-11); 0.98 s (3H, Me-ketal); 0.97 s (3H,Me-ketal); 0.90 s (3H,C-18)

b) 9,11α-Dihydro-17α-ethinyl-17β-hydroxy-6'H-benzo[10,9,11]estr-4-en-3-one

According to general instruction 1), 1.2 g of 2a) is reacted with 3 ml of 4 n hydrochloric acid in acetone. After crystallization of the crude product from ethyl acetate, 776 mg of 2b) is obtained as white crystals.

$^1$H-NMR (CDCl$_3$): δ=5.81 ppm sbr (1H,H-4); 5.62 dbr (J=10 Hz,1H,Bridge); 5.56 m (1H,Bridge); 2.67 m (1H,H-11); 2.59 s (1H,ethine); 0.91 s (3H,C-18)

Example 3

9,11αDihydro-17β-hydroxy-17α-(1-propinyl)-6'H-benzo[10,9,11]estr-4-en-3-one a) 9,11α-Dihydro-3,3-[2,2-dimethyl-1,3-propanediylbis(oxy)]-17α-(1-propinyl)-6'H-benzo[10,9,11]-5α-estrane-5,17β-diol According to general instruction 2), 1 g of the compound described under 1c) and 15.1 ml of a 1.6 molar solution of n-butyllithium in hexane as well as propine gas in absolute tetrahydrofuran are reacted. 1.05 g of 3a) is obtained as white foam, which is used without purification in the next stage.

3b) 9,11α-Dihydro-17β-hydroxy-17α-(1-propinyl)-6'H-benzo[10,9,11]estr-4-en-3-one According to general instruction 1), 1 g of the substance described under 3a) is reacted with 2.5 ml of 4 n aqueous hydrochloric acid in acetone. After crystallization of the crude product from diisopropyl ether, 600 mg of 3b) is obtained as white crystals.

Melting point=161.6° C.; $[α]_D^{20}$=−53.4° (CHCl$_3$; c=0.520)

$^1$H-NMR (CDCl$_3$): δ=5.81 ppm sbr (1H,H-4); 5.60 dbr (J=10 Hz,1H,Bridge); 5.50 m (1H,Bridge); 2.68 m (1H,H-11); 1.87 s (3H,propine); 0.90 s (3H,C-18)

Example 4

(Z)-9,11α-Dihydro-17β-hydroxy-17α-(3-hydroxy-1-propenyl)-6'H-benzo[10,9,11]estr-4-en-3-one a) 9,11α-Dihydro-3,3-[2,2-dimethyl-1,3-propanediylbis(oxy))]-17α-[3-[(tetrahydro-2H-pyran-2-yl)oxy]-1-propinyl]-6'H-benzo[10,9,11]-5α-estrane-5,17β-diol The lithium-organic compound is produced from 17 ml of 3-[(tetrahydro-2H-pyran-2-yl)oxy]-1-propine in 600 ml of absolute tetrahydrofuran and 75.4 ml of a 1.6 molar solution of n-butyllithium in hexane at 0° C. under argon. Then, a solution of 5 g of the substance described under 1e), in 120 ml of absolute tetrahydrofuran, is added. It is allowed to stir for one more hour at 0° C. and then aqueously worked up (C, F). After purification, 5.75 g of 4a) is obtained as white foam.

¹H-NMR (CDCl₃): δ=5.56 ppm dbr (J=10 Hz, 1H,Bridge); 5.48 m (1H,Bridge); 4.84 m (1H,THP); 4.40 s (1H,OH); 4.32 m (2H,CH₂OTHP); 3.87 m (1H,THP); 3.50–3.70 m (5H,ketal and THP); 2.50 m (1H,H-11); 0.095 m (6H,Me-ketal); 0.89 s (3H,C-18)

b) (Z)-9,11α-Dihydro-3,3-[2,2-dimethyl-1,3-propanediylbis(oxy)]-17α-[3-[(tetrahydro-2H-pyran-2-yl)oxy]-I-propenyl]-6'H-benzo[10,9,11]-5α-estrane-5,17β-diol 549 mg of palladium on barium sulfate (10%) is added to a solution of 5.4 g of the substance, described under 4a), in 45 ml of tetrahydrofuran. The apparatus is placed under hydrogen and allowed to stir for 20 minutes. Then, the reaction mixture is filtered on Celite and concentrated by evaporation in a vacuum. After purification, 4.56 g of 4b) is obtained as white foam.

¹H-NMR (CDCl₃): δ=5.73 ppm dbr (J=10 Hz, 1H,Bridge); 5.55 m (2H); 5.47 m (1H,Bridge); 4.71 m (1H,THP); 4.38 m (2H,CH₂OTHP); 3.85 m (1H,THP); 3.50–3.65 m (5H,ketal and THP); 2.45 m (1H,H-11); 0.99 s (3H,Me-ketal); 0.98 s (3H,Me-ketal); 0.94 s (3H,C-18)

c) (Z)-9,11α-Dihydro-17β-hydroxy-17α-(3-hydroxy-1-propenyl)-6'H-benzo[10,9,11]estr-4-en-3-one According to general instruction 1), 1 g of the substance described under 4b) is reacted with 4 n hydrochloric acid in acetone. After crystallization of the crude product from diisopropyl ether, 440 mg of 4c) is obtained as white crystals.

Melting point=219°–221° C.; $[\alpha]_D^{20}$=21.3° (CHCl₃, c=0.535)

¹H-NMR (CDCl₃): δ=5.81 ppm sbr (1H,H-4); 5.70 m (1H); 5.62 dbr (J=10 Hz,1H,Bridge); 5.59 m (2H); 4.26 m (2H,CH₂OH); 2.63 m (1H,H-11); 1.00 s (3H,C-18)

Example 5

9,11α-Dihydro-17β-hydroxy-17α-(3-hydroxypropyl)-6'H-benzo[10,9,11]estr-4-en-3-one a) 9,11α-Dihydro-3,3-[2,2-dimethyl-1,3-propanediylbis(oxy)]-17α-[3-[(tetrahydro-2H-pyran-2-yl)oxy]propyl]-6'H-benzo[10,9,11]-5α-estrane-5,17β-diol 360 mg of palladium on activated carbon (10%) is added to a solution of 3.56 g of the substance, described under 4b), in 175 ml of ethyl acetate. The apparatus is placed under hydrogen and allowed to stir for 1 more hour at room temperature. Then, the reaction mixture is filtered on Celite and concentrated by evaporation in a vacuum. The obtained crude product (3.49 g) is used without purification in the next stage.

b) 9,11α-Dihydro-17β-hydroxy-17α-(3-hydroxypropyl)-6'H-benzo[10,9,11]estr-4-en-3-one According to general instruction 1), 3.23 g of 5a) is reacted with 4 n hydrochloric acid in acetone. After purification, 1.5 g of 5b) is obtained as white foam.

$[\alpha]_D^{20}$=–23.7° (CHCl₃; c=0.510)

¹H-NMR (CDCl₃): δ=5.81 ppm sbr (1H,H-4); 5.63 dbr (J=10 Hz,1H,Bridge); 5.50 m (1H,Bridge); 3.60–3.75 m (2H,CH₂OH); 2.68 m (1H,H-11); 0.96 s (3H,C-18)

Example 6

5",4",9,11α-Tetrahydrospiro[6'H-benzo[10,9,11]estr-4-ene-17β,2"(5")-furan]-3,5"-dione According to general instruction 3), 700 mg of the substance described under 5b), 1.1 g of chromium trioxide and 3.62 ml of pyridine in dichloromethane are reacted. After purification, 485 mg of 6) is obtained as white foam.

$[\alpha]_D^{20}$=–31.4° (CHCl₃; c=0.515)

¹H-NMR (CDCl₃): δ=5.82 ppm sbr (1H,H-4); 5.58 m (2H,Bridge); 2.71 m (1H,H-11); 1.02 s (3H,C-19)

Example 7

5",4",9,11α-Tetrahydrospiro[6'H-benzo[10,9,11]estr-4-ene-17β,2"(5")-furan]-3-one 600 mg of the compound described under 5b) is dissolved in 40 ml of dichloromethane. It is mixed with 3.3 ml of triethylamine. It is cooled to 0° C. and 770 mg of p-toluenesulfonic acid chloride is added. Then, it is allowed to stir for one more hour at 0° C. and for 6 hours at room temperature, and then aqueously worked up (B. F). After purification, 380 mg of 7) is obtained as white foam.

¹H-NMR (CDCl₃): δ=5.82 ppm sbr (1H,H-4); 5.62 dbr (J=10 Hz,1H,Bridge); 5.55 m (1H,Bridge); 3.70–3.81 m (2H,spiro ether); 2.63 m (1H,H-11); 0.93 s (3H,C-18)

Melting point=127.3° C., $[\alpha]_D^{20}$=–52.3 (CHCl₃; c=0.485)

Example 8

9,11α-Dihydro-17β-hydroxy-17α-(1,3-pentadiinyl)-6'H-benzo[10,9,11]estr-4-en-3-one 700 mg of the substance described under 2b) is dissolved in 60 ml of triethylamine. The solution is saturated at room temperature with propine gas, 250 mg of tetrakis(triphenylphosphine)palladium and 120 mg of copper (I) iodide are added, heated to 60° C. and, while maintaining the propine stream, allowed to stir for one more hour at this temperature. Then, the reaction solution is filtered on Celite and concentrated by evaporation in a vacuum. After purification, 311 mg of 8) is obtained as white foam.

¹H-NMR (CDCl₃): δ=5.80 ppm sbr (1H,H-4); 5.58 m (2H,Bridge); 2.70 m (1H,H-11); 1.95 s (3H,butinyl); 0.82 s (3H,methyl)

Example 9

9,11α-Dihydro-17α-ethinyl-17β-hydroxy-6'H-benzo[10,9,11]estra-4,15-dien-3-one a) 9,11α-Dihydro-3,3-[2,2-dimethyl-1,3-propanediylbis(oxy)]-17-[(trimethylsilyl)oxy]-6'H-benzo[10,9,11]-5α-estr-16-en-5-ol According to general instruction 4a), 2.7 g of the substance described under 1e) is reacted with 3.2 ml of diisopropylamine, 14.4 ml of a 1.6 molar solution of n-butyllithium in hexane and 4 ml of trimethylchlorosilane in absolute tetrahydrofuran. After recrystallization of the crude product from acetonitrile, 2.5 g of 9a) is obtained.

b) 9,11α-Dihydro-3,3-[2,2-dimethyl-1,3-propanediylbis(oxy)]-5-hydroxy-6'H-benzo[10,9,11]-5α-estr-15-en-17-one According to general instruction 4b), 2.5 g of the compound described under 9a) is reacted with 1.3 g of palladium(II) acetate in acetonitrile. After purification, 1.8 g of 9b) is obtained.

¹H-NMR (CDCl₃): δ=7.52 ppm dbr (J=6 Hz,1H,H-15); 5.98 dd (J=6.3HZ, 1H,H-16); 5.60 dbr (J=10 Hz, 1H,Bridge); 5.50 m (1H,Bridge); 4.47 s (3H,OH); 3.50–3.60 m (4H,ketal); 2.60 m (1H,H-11); 1.18 s (3H,C-18); 1.00 s (3H,Me-ketal); 0.98 s (3H, Me-ketal)

c) 9,11α-Dihydro-3,3-[2,2-dimethyl-1,3-propanediylbis(oxy)]-17α-ethinyl-6'H-benzo[10,9,11]-5α-estr-15-ene-5,17β-diol According to general instruction 2), 1.8 g of 9b), 15 ml of a 1.6 molar solution of n-butyllithium in hexane as well as ethine gas in absolute tetrahydrofuran are reacted. 1.59 g of 9c) is obtained, which is used without purification in the next stage.

d) 9,11α-Dihydro-17α-ethinyl-17β-hydroxy-6'H-benzo[10,9,11]estra-4,15-dien-3-one According to general instruction 1), 1.59 g of 9c) is reacted with 4 n hydrochloric acid in acetone. After purification, 970 mg of 9d) is obtained.

$^1$H-NMR (CDCl$_3$): δ=6.00 dbr (J=6 Hz, 1H,H-15); 5.72 sbr(1H,H-4); 5.21 dd (J=6.3 Hz, 1H,H-16); 5.60 m (2H, Bridge); 2.77 m (1H,H-11); 2.60 s (1H, ethine); 1.00 s (3H,C-18)

Melting point=198° C., $[α]_D^{20}$=–202.9° (CHCl$_3$; c=0.515)

Example 10

9,11α-Dihydro-17β-hydroxy-17α-(1-propinyl)-6'H-benzo[10,9,11]estra-4,15-dien-3-one a) 9,11α-Dihydro-3,3-[2,2-dimethyl-1,3-propanediylbis(oxy)]-17α-(1-propinyl)-6'H-benzo[10,9,11]-5α-estr-15-ene-5,17β-diol According to general instruction 2), 1g of 9b), 15 ml of a 1.6 olar solution of n-butyllithium in hexane as well as propine gas in absolute tetrahydrofuran are reacted. 1 g of 10a) is obtained, which is used without purification in the next stage.

b) 9,11α-Dihydro-17β-hydroxy-17α-(1-propinyl)-6'H-benzo[10,9,11]estra-4,15-dien-3-one According to general instruction 1), 1 g of 10a) is reacted with 4 n hydrochloric acid in acetone. After purification, 610 mg of 10b) is obtained.

$[α]_D^{20}$=–204.2° (CHCl$_3$; c=0.520)

$^1$H-NMR (CDCl$_3$): δ=5.94 dbr (J=6 Hz,1H,H-15); 5.72 sbr (1H,H-4); 5.20 dd (J=6.3 Hz,1H,H-16); 5.60 m (2H, Bridge); 2.73 m (1H,H-11); 1.90 s (3H,propine); 0.99 s (3H,C-18)

Example 11

9,11α-Dihydro-17β-hydroxy-17α-methyl-6'H-benzo[10,9,11]estra-4,14-dien-3-one a) 9,11α-Dihydro-3,3-[2,2-dimethyl-1,3-propanediylbis(oxy)]-5-hydroxy-6'H-benzo[10,9,11]-5α-estr-14-en-17-one 2.3 g of the substance described under 9b) is dissolved in 300 ml of a mixture of ethyl acetate and hexane (9:1). 180 g of silica gel and 35 ml of triethylamine are added and it is allowed to stir for 2 more days at room temperature. Then, it is filtered on Celite and concentrated by evaporation. 1.02 g of a) in addition to 1.15 g of initial material are obtained.

$^1$H-NMR (CDCl$_3$): δ=5.65 ppm dbr (J=10 Hz,1H,Bridge); 5.55 m (1H,Bridge); 5.52 m (1H,H-15); 4.40 s (1H,OH); 3.50–3.62 m (4H,ketal); 3.00 ddd (J=20,3.1 Hz,1H,H-16); 2.80 dt (J=20,1.5 Hz,1H,H-16'); 2.51 m (1H,H-11); 1.12 s (3H,C-18); 1.00 s (3H,Me-ketal); 0.98 s (3H,Me-ketal)

b) 9,11α-Dihydro-3,3-[2,2-dimethyl-1,3-propanediylbis(oxy)]-17α-methyl-6'H-benzo [10,9,11]-5α-estr-14-ene-5,17β-diol 2.5 g of anhydrous cerium trichloride is added to 20 ml of absolute tetrahydrofuran. The suspension is allowed to stir for one more hour, then cooled to 0° C. and 3.34 ml of a 3 molar solution of methyl magnesium chloride in absolute tetrahydrofuran is added. It is allowed to stir for another 1.5 hours at 0° C. and then a solution of 413 mg of the substance, described under 11a), in 5 ml of absolute tetrahydrofuran is added. Then, it is stirred for 30 more minutes at 0° C. and then aqueously worked up (C, F). After purification, 170 mg of 11b) is obtained.

$^1$H-NMR (CDCl$_3$): δ=5.60 ppm dbr (J=10 Hz, 1H,Bridge); 5.52 m (1H,Bridge); 5.18 m (1H,H-15); 4.40 s (1H,OH); 3.50–3.62 m (4H,ketal); 2.52 m (1H,H-11); 2.42 dtr (J=10,1 Hz,1H,H-16); 2.30 dtr (J=20,1 Hz,1H,H-16'); 1.22 s (3H,17-methyl); 1.10 s (3H,C-18); 0.98 s (6H,Me-ketal)

c) 9,11α-Dihydro-17β-hydroxy-17α-methyl-6'H-benzo[10,9,11]estra-4,14-dien-3-one

According to general instruction 1, 170 mg of the compound described under 11b) is reacted with 4 n hydrochloric acid in acetone. After purification, 100 mg of 11c) is obtained.

$[α]_D^{20}$=–38.020 (CHCl$_3$; C=0.505)

$^1$H-NMR (CDCl$_3$): δ=5.83 sbr (1H,H-4); 5.68 dbr (J=10 Hz,1H,Bridge); 5.62 m (1H,Bridge); 5.18 m (1H,H-15); 1.23 s (3H,17-methyl); 1.13 s (3H,C-18)

Example 12

9,11α,1-Dihydro-17β-hydroxy-17α-(1-propinyl)-6'H-benzo[10,9,11]estra-4,14,dien-3-one a) 9,11α-Dihydro-3,3-[2,2-dimethyl-1,3-propanediylbis(oxy)]-17α-(1-propinyl)-6'H-benzo-[10,9,11]-5α-estr-14-ene-5,17β-diol According to general instruction 2), a saturated solution of propine gas in 30 ml of absolute tetrahydrofuran is reacted with 6.25 ml of a 1.6 molar solution of n-butyllithium in hexane. This solution is added to a suspension of 2.5 g of anhydrous cerium trichloride in 20 ml of absolute tetrahydrofuran, which was pretreated analogously to example 11b). Then, it is reacted analogously to 11b) with a solution of 413 mg of the substance, described under 11a), in absolute tetrahydrofuran. 420 mg of crude product is obtained, which is used without purification in the next stage.

b) 9,11α-Dihydro-17β-hydroxy-17α-(1-propinyl)-6'H-benzo[10,9,11]estra-4,14-dien-3-one According to general instruction 1), 420 mg of 12a) is reacted with 4 n hydrochloric acid in acetone. After purification, 200 mg of 12b) is obtained as white foam.

$^1$H-NMR (CDCl$_3$): δ=5.82 ppm sbr (1H,H-4); 5.69 dbr (J=10 Hz,1H,Bridge); 5.62 m (1H,Bridge); 5.15 m (1H,H-15); 1.88 s (3H,propine); 1.15 s (3H,C-18)

Example 13

17-(Acetyloxy)-9,11α-dihydro-6'H-benzo[10,9,11]-19-norpregn-4-ene-3,20-dione a) 9,11α-Dihydro-5,17α-dihydroxy-3,3-[2,2-dimethyl-1,3-propanediylbis(oxy)]-6'H-benzo[10,9,11]-5α-estranα-17β-carbonitrile 10 g of the substance described under 1e) is dissolved in 50 ml of 2-hydroxy-2-methylpropanenitrile together with 0.74 ml of 20% aqueous sodium hydroxide solution at 80° C. The product precipitated after cooling is filtered off and recrystallized from diisopropyl ether. 8.6 g of 13a) is obtained as white crystals.

$^1$H-NMR (CDCl$_3$): δ=5.58 ppm dbr (J=10 Hz,1H,Bridge); 5.50 m (1H,Bridge); 4.60 (1H,OH); 3.50–3.62 m (4H,ketal); 2.59 m (1H,H-11); 1.00 s (3H,Me-ketal); 0.97 s (3H,Me-ketal); 0.96 s (3H,C-18)

b) 9,11α-Dihydro-17-hydroxy-6'H-benzo[10,9,11]-19-norpregn-4-ene-3,20-dione 350 mg of p-toluenesulfonic acid and 8.8 ml of ethoxyethene are added to a solution of 4 g of the compound, described under 13a), in 100 ml of diethyl ether. It is allowed to stir for 30 more minutes at room temperature and then aqueously worked up (B, F). The obtained crude product is again dissolved in 100 ml of diethyl ether. It is cooled to 0° C. and 16 ml of a 1.6 molar solution of methyllithium in diethyl ether is added. It is allowed to stir for 3 more hours at 0° C. and then aqueously worked up (C, F). The obtained crude product is reacted according to general instruction 1). After crystallization from diisopropyl ether/methanol, 2.9 g of 13b) is obtained as white crystals.

$^1$H-NMR (CDCl$_3$): δ=5.81 ppm sbr (1H,H-4); 5.55 m (2H,Bridge); 2.27 s (3H,acetyl); 0.71 s (3H,C-18)

13c) 17-(Acetyloxy)-9,11α-dihydro-6'H-benzo[10,9,11]-19-norpregn-4-ene-3,20-dione 15 ml of trifluoroacetic acid anhydride is added to a suspension of 2.9 g of the substance, described under 13b), in 40 ml of glacial acetic acid at 0° C. It is allowed to stir for 4 more hours at room temperature and then aqueously worked up (B, F). After purification, 2.3 g of 13c) is obtained.

Melting point=223° C., [α]$_D^{20}$=−29.3° (CHCl$_3$; C=0.515)
$^1$H-NMR (CDCl$_3$): δ=5.82 ppm sbr (1H,H-4); 5.56 m (2H,Bridge); 2.72 m (1H,H-11); 2.15 s (3H,acetyl); 2.10 s (3H,acetoxy); 0.70 s (3H,C-18)

Example 14

17-(Acetyloxy)-9,11α-dihydro-6'H-benzo[10,911]-19-norpregna-4,6-diene-3,20-dione a) 17-(Acetyloxy)-9,11α-dihydro-3-ethoxy-6'H-benzo[10,9,11]-19-norpregna-3,5-dien-20-one A mixture of 800 mg of the substance described under 13c), 2 ml of triethylorthoformate, 2 ml of ethanol and 40 mg of p-toluenesulfonic acid in 20 ml of tetrahydrofuran is stirred for one hour at 40° C. Then, it is aqueously worked up (B, F). The obtained crude product (850 mg) is used without purification in the next stage.

b) 17-(Acetyloxy)-6β-bromo-9,11α-dihydro-6'H-benzo[10,9,11]-19-norpregn-4-ene-3,20-dione 4 ml of 10% aqueous sodium acetate solution and then 285 mg of 1,3-dibromo-5,5-dimethylhydantoin are added to a solution of 850 mg of the substance, described under 14a), in 10 ml of dioxan. It is allowed to stir for 5 more minutes at 0° C. and it is then aqueously worked up (B, F). After purification, 600 mg of 14b) is obtained.

$^1$H-NMR (CDCl$_3$): δ=6.02 ppm sbr (1H,H-4); 5.60 m (1H,Bridge); 5.52 dbr (J=10 Hz,1H,Bridge); 5.05 dbr (J=4 Hz,1H,H-6α); 2.28 m (1H,H-11); 2.15 s (3H,acetyl); 2.10 s (3H,acetoxy); 0.79 s (3H,C-18)

c) 17-(Acetyloxy)-9,11α-dihydro-6'H-benzo[10,9,11]-19-norpregna-4,6-diene-3,20-dione A mixture of 600 mg of the substance described under 14b), 550 mg of lithium bromide and 375 mg of lithium carbonate in 10 ml of N,N-dimethylformamide is stirred for one hour at 100° C. Then, it is aqueously worked up (A, F). After purification, 435 mg of 14c) is obtained.

[α]$_D^{20}$=−35.5° (CHCl$_3$; c=0.520)
$^1$H-NMR (CDCl$_3$): δ=6.13 ppm m (2H,H-6'H-7); 5.73 sbr (1H,H-4); 5.60 m (2H,Bridge); 2.79 m (1H,H-11); 2.15 s (3H,acetyl); 2.10 s (3H,acetoxy); 0.73 s (3H,C-18)

Example 15

17-(Acetyloxy)-6-chloro-9,11α-dihydro-6'H-benzo[10,9,11]-19-norpregna-4,6-diene-3,20-dione a) 17-(Acetyloxy)-9,11α-dihydro-6α,7α-epoxy-6'H-benzo[10,9,11]-19-norpregn-4-ene-3,20-dione 1.8 g of m-chloroperbenzoic acid (70%) is added to a solution of 2 g of the compound, described under 14c), in 50 ml of dichloromethane. It is allowed to stir for 8 more hours at room temperature. Then, the reaction mixture is poured on saturated aqueous sodium bicarbonate solution, extracted with dichloromethane and the organic phase is washed with saturated sodium thiosulfate as well as saturated sodium chloride solution. Purification produces 832 mg of 15a).

$^1$H-NMR (CDCl$_3$): δ=6.20 s (1H,H-4); 5.55 m (2H, Bridge); 3.52 d (J=4 Hz,1H,H-6); 3.45 dbr (J=4 Hz,1H,H-7); 2.70 m (1H,H-11); 2.15 s (3H,acetyl); 2.10 s (3H,acetoxy); 0.73 s (3H,C-18)

b) 17-(Acetyloxy)-6β-chloro-9,11α-dihydro-7α-hydroxy-6'H-benzo[10,9,11]-19-norpregn-4-ene-3,20-dione 4.8 g of lithium chloride is added to a solution of 832 mg of the compound, described under 15a), in 20 ml of glacial acetic acid. It is stirred for 1.5 more hours and then aqueously worked up (B, F). The obtained crude product (900 mg) is used without purification in the next stage.

c) 17-(Acetyloxy)-6β-chloro-9,11α-dihydro-7α-[(methylsulfonyl)oxy]-6'H-benzo[10,9,11]-19-norpregn-4-ene-3,20-dione 1.2 ml of methanesulfonic acid chloride is added to a solution of 900 mg of the substance, described under 15b), in 10 ml of pyridine at 0° C. It is stirred for two more hours at room temperature, then the reaction mixture is poured on saturated aqueous sodium chloride solution and extracted with dichloromethane. The organic phase is washed with saturated sodium chloride solution. The obtained crude product is used without purification in the next stage.

d) 17-(Acetyloxy)-6-chloro-9,11α-dihydro-6'H-benzo[10,9,11]-19-norpregna-4,6-diene-3,20-dione 3.5 g of anhydrous sodium acetate is added to a solution of 930 mg of the substance, described under 15c), in 25 ml of N,N-dimethylformamide. It is heated to 100° C. and allowed to stir for 1.5 more hours at this temperature. Then, the reaction mixture is poured on ice water. It is allowed to stir for another hour and then the precipitate is filtered off. After purification of the crude product, 450 mg of 15d) is obtained.

Melting point=225° C., [α]$_D^{20}$=−39.2° (CHCl$_3$; c=0.505)
$^1$H-NMR (CDCl$_3$): δ=6.40 ppm sbr (1H,H-4); 6.35 d (J=2 Hz,1H,H-7); 5.60 m (2H,Bridge); 2.80 m (1H,H-11); 2.13 s (3H,acetyl); 2.09 s (3H,acetoxy); 0.72 s (3H,C-18)

Example 16

17-(Acetyloxy)-9,11α-dihydro-β-methylene-6'H-benzo[10,9,11]-19-norpregn-4-ene-3,20,dione 3 g of the substance described under example 13c) is dissolved in 75 ml of tetrahydrofuran. 7.5 ml of ethanol, 7.5 ml of triethylorthoformate and 170 mg of p-toluenesulfonic acid are added. Then, it is stirred for one hour at 40° C. Then, 2.3 ml of N-methylaniline and 2.6 ml of 37% aqueous formaldehyde solution are added. It is stirred for another 30 minutes at 40° C. Then, it is allowed to cool to room temperature and 7.5 ml of concentrated hydrochloric acid is added. It is allowed to stir for another 3 hours at room temperature and is aqueously worked up (A, E, F). After purification, 2 g of 16) is obtained.

$^1$H-NMR (CDCl$_3$): δ=6.02 ppm sbr (1H,H-4); 5.55 m (2H,Bridge); 5.15 m (1H,exo-methylene), 5.02 m (1H,exo-methylene); 2.76 m (1H,H-11); 2.13 s (3H,acetyl); 2.10 s (3H,acetoxy); 0.72 s (3H,C-18)

Example 17

17-(Acetyloxy)-9,11α-dihydro-6α-methyl-6'H-benzo[10,9,11]-19-norpregn-4-ene-3,20-dione 2 g of the substance described under 16) is dissolved in 30 ml of ethanol. 3 ml of cyclohexene and 250 mg of palladium on activated carbon (10%) are added. Then, it is refluxed for one hour. Then, the reaction solution is filtered on Celite. It is concentrated by evaporation in a vacuum, the residue is taken up in 30 ml of acetone, 1.4 ml of 4 n hydrochloric acid is added and stirred for 2.5 more hours at 40° C. Aqueous working up (B, F) and purification produces 1.1 g of 17).

Melting point=248° C., $[\alpha]_D^{20}$=−39.4° (CHCl$_{13}$; c=0.510)

$^1$H-NMR (CDCl$_3$): δ=5.90 ppm sbr (1H,H-4); 5.57 m (2H,Bridge); 2.73 m (1H,H-11); 2.13 s (3H,acetyl); 2.09 s (3H,acetoxy); 1.12 d (J=6 Hz,3H,6α-methyl); 0.72 s (3H, C-18)

Example 18

17-(Acetyloxy)-9,11α-dihydro-β-methyl-6'H-benzo[10,9, 11]-19-norpregna-4,6-diene-3,20-dione 125 mg of palladium on activated carbon (10%) is added to 0.25 ml of cyclohexene in 15 ml of ethanol. It is refluxed for one hour and then a solution of 500 mg of the substance, described under example 16), in 5 ml of ethanol is added. Then, it is refluxed for another two hours. Then, it is filtered on Celite and concentrated by evaporation in a vacuum. After purification, 400 mg of 18) is obtained.

Melting point=203° C., $[\alpha]_D^{20}$=+28.1° (CHCl$_3$;c=0.515)

$^1$H-NMR (CDCl$_3$): δ=6.00 ppm sbr (1H,H-7); 5.92 sbr (1H,H-4); 5.60 m (2H,Bridge); 2.77 m (1H,H-11); 2.14 s (3H,acetyl); 2.10 s (3H,acetoxy); 1.88 sbr (3H,β-methyl); 0.73 s (3H,C-18)

Example 19

17β-Hydroxy-17α-methyl-4',5',9,11α-tetrahydro-6'H-benzo[10,9,11]estr-4-en-3-one a) 3,3-[2,2-Dimethyl-1,3-propanediylbis(oxy)]-5-hydroxy-4',5',9,11α-tetrahydro-6'H-benzo[10,9,11]-5α-estran-17-one Hydrogenation with Use of palladium on Activated Carbon:

165 mg of palladium on activated carbon (10%) is added to a solution of 1.6 g of the substance, described under 1e), in 65 ml of ethanol. The apparatus is placed under 15 bars of hydrogen pressure and allowed to react for two hours. Then, it is filtered on Celite and concentrated by evaporation in a vacuum. 1.5 g of 19a) is obtained, which is further used without purification.

Hydrogenation with Use of platinum Oxide:

100 mg of platinum(IV) oxide is added to a solution of 1 g of the substance, described in 1e), in a mixture of 24 ml of ethyl acetate and 6 ml of tetrahydrofuran. The apparatus is placed under hydrogen and allowed to stir for one more hour at room temperature. Then, the reaction solution is filtered on Celite and concentrated by evaporation. After purification, 600 mg of 19a) and 150 mg of 3,3-[2,2-dimethyl-1,3-propanediylbis(oxy)]-4',5',9,11α-tetrahydro-6'H-benzo[10,9,11]-5α-estranα-5,17β-diol are obtained.

$^1$H-NMR (CDCl$_3$): δ=4.30 ppm s (1H,OH); 3.50–3.60 m (4H,ketal); 2.40 dd (J=17.9 Hz,1H,H-16); 1.00 s (3H,C-18); 0.96 s (3H,Me-ketal); 0.94 s (3H,Me-ketal)

b) 3,3-[2,2-Dimethyl-1,3-propanediylbis (oxy) ]-17α-methyl-4',5',9,11α-tetrahydro-6'H-benzo[10,9,11]-5α-estrane-5,17β-diol Analogously to example 1f), 1.65 g of the substance, produced under 19a), in 30 ml of absolute tetrahydrofuran is reacted with 18.8 ml of a 1.6 molar solution of methyllithium in diethyl ether. 1.5 g of 19b) is obtained, which is used without purification in the next stage.

c) 17β-Hydroxy-17α-methyl-4',5',9,11α-tetrahydro-6'H-benzo[10,9,11]estr-4-en-3-one According to general instruction 1, 1.5 g of the substance described under 19b) is reacted with 4 n hydrochloric acid in acetone. After purification, 0.97 g of 19c) is obtained as white foam.

$[\alpha]_D^{20}$=+107.8° (CHCl$_3$; C=0,520)

$^1$H-NMR (CDCl$_3$): δ=5.75 ppm sbr (1H,H-4); 1.22 s (3H,methyl); 1.03 s (3H,C-19)

Example 20

17β-Hydroxy-17α-(1-propinyl)-4',5',9,11α-tetrahydro-6'H-benzo[10,9,11]estr-4-en-3-one a) 3,3-(2,2-Dimethyl-1,3-propanediylbis(oxy)]-17α-(1-propinyl)-4',5',9,11α-tetrahydro-6'H-benzo[10,9,11]-5α-estranα-5,17β-diol According to general instruction 2), 1 g of the compound described under 19a) and 15 ml of a 1.6 molar solution of n-butyllithium in hexane as well as propine gas in absolute tetrahydrofuran are reacted. The obtained crude product (1.19 g) is used without purification in the next stage.

b) 17β-Hydroxy-17α-(1-propinyl)-4',5',9,11α-tetrahydro-6'H-benzo[10,9,11]estr-4-en-3-one According to general instruction 1), 1.19 g of 20a) is reacted with 4 n hydrochloric acid in acetone. After purification, 720 mg of 20b) is obtained.

Melting point=186.7° C., $[\alpha]_D^{20}$+70.1° (CHCl$_3$; c=0.510)

$^1$H-NMR (CDCl$_3$): δ=5.73 ppm s (1H,H-4); 1.84 s (3H, propine); 1.01 s (3H,C-18)

Example 21

17β-Hydroxy-17α-(1-propinyl)-4',5',9,11α-tetrahydro-6'H-benzo[10,9,11]-estra-4,15-dien-3-one a) 3,3-[2,2-Dimethyl-1,3-propanediylbis(oxy)]-4',5',9, 11α-tetrahydro-17-[(trimethylsilyl)oxy]-6'H-benzo[10,9, 11]-estr-16-en-5-ol According to general instruction 4a), 1 g of the compound described under 19a) is reacted with 1.2 ml of diisopropylamine, 5.6 ml of a 1.6 molar solution of n-butyllithium in hexane and 1.5 ml of trimethylchlorosilane in absolute tetrahydrofuran. After recrystallization of the crude product from acetonitrile, 940 mg of 21a) is obtained.

b) 3,3-[2,2-Dimethyl-1,3-propanediylbis(oxy)]-5-hydroxy-4',5',9,11α-tetrahydro-6'H-benzo[10,9,11]-5α-estr-15-en-17-one According to general instruction 4b), 940 mg of 21a) is reacted with 475 mg of palladium(II) acetate in acetonitrile. After purification, 650 mg of 21b) is obtained.

$^1$H-NMR (CDCl$_3$): δ=7.52 ppm dbr (J=6 Hz,1H,H-15); 5.96 dd (J=6.3 Hz,1H,H-16); 4.45 s (1H,OH); 3.50–3.60 m (4H,ketal); 1.21 s (3H,C-18); 1.00 s (3H,Me-ketal); 0.97 s (3H,Me-ketal)

c) 3,3-[2,2-Dimethyl-1,3-propanediylbis(oxy)]-17α-(1-propinyl)-4',5',9,11α-tetrahydro-6'H-benzo[10,9,11]-5α-estr-15-ene-5,17β-diol According to general instruction 2), 712 mg of 21c) is obtained from 650 mg of 21b), 10 ml of a 1.6 molar solution of n-butyllithium in hexane as well as propine gas in absolute tetrahydrofuran. The crude product is used without purification in the next stage.

d) 17β-Hydroxy-17α-(1-propinyl)-4',5',9,11 α-tetrahydro-6'H-benzo[10,9,11]-estra-4,15-dien-3-one According to general instruction 1), 712 mg of 21c) is reacted with 4 n hydrochloric acid in acetone. After purification, 440 mg of 21d) is obtained.

$[\alpha]_D^{20}$=−79.6°(CHCl$_3$; c=0.510)

$^1$H-NMR (CDCl$_3$): δ=5.98 ppm dbr (J=6 Hz,1H,H-15); 5.76 sbr (1H,H-4), 5.70 dd (J=6.3 Hz,1H,H-16); 1.90 s (3H,propine); 1.09 s (3H,C-18)

Example 22

5',6'-Dihydro-17β-hydroxy-17α-(1-propinyl)-9H-benzo[10,9,11]-estr-4-en-3-one a)   5',6'-Dihydro-3,3-[2,2-dimethyl-1,3-propanediyl-bis(oxy)]-5-hydroxy-9H-benzo-[10,9,11]-5α-estran-17-one 4 g of the substance described under 1e) is dissolved in 120 ml of a mixture of tetrahydrofuran and ethanol (1;1). 25 ml of cyclohexene and 1 g of palladium on activated carbon (10%) are added and refluxed for 24 hours. Then, it is filtered on Celite and concentrated by evaporation in a vacuum. After purification, 1.8 g of 22a) is obtained.

$^1$H-NMR (CDCl$_3$): δ=5.29 ppm m (1H,Bridge/11-exo); 4.40 s (1H,OH); 3.50–3.60 m (4H,ketal); 2.43 dd (J=17.9 Hz,1H,H-16); 1.00 s (3H,Me-ketal); 0.98 s (3H,Me-ketal); 0.80 s (3H,C-18)

b)   5',6'-Dihydro-3,3-[2,2-dimethyl-1,3-propanediyl-bis(oxy)]-17α-(1-propinyl)-9H-benzo[10,9,11]-5α-estrana-5,17β-diol According to general instruction 2), 1.1 g of 22b) is obtained as crude product from 1 g of the substance described under 22a) and 15 ml of a 1.6 molar solution of n-butyllithium in hexane as well as propine gas in absolute tetrahydrofuran, crude product which is used without purification in the next stage.

c)   5',6'-Dihydro-17β-hydroxy-17a-(1-propinyl)-9H-benzo[10,9,11]estr-4-en-3-one According to general instruction 1, 1.1 g of the substance described under 22b) is reacted with 4 n hydrochloric acid in acetone. After purification, 640 mg of 22c) is obtained.

Melting point=197.3° C., $[\alpha]_D^{20}$=+40.7° (CHCl$_3$; c=0.520)

$^1$H-NMR (CDCl$_3$): δ=5.27 ppm sbr (1H,H-4); 5.48 (1H,Bridge/11-exo); 1.86 s (3H,propine); 0.80 s (3H,C-18)

Example 23

5',6'-Dihydro-17β-hydroxy-17α-(1-propinyl)-9H-benzo[10,9,11]estra-4,15-dien-3-one a)   5',6'-Dihydro-3,3-[2,2-dimethyl-1,3-propanediyl-bis(oxy)]-17-[(trimethylsilyl)oxy]-9H-benzo [10,9,11]-5α-estr-16-en-5-ol According to general instruction 4a), 1 g of the substance described under 22a) is reacted with 1.2 ml of diisopropylamine, 5.6 ml of a 1.6 molar solution of n-butyllithium in hexane and 1.5 ml of trimethylchlorosilane in absolute tetrahydrofuran. After recrystallization of the crude product from acetonitrile, 920 mg of 23a) is obtained.

b)   5',6'-Dihydro-3,3-[2,2-dimethyl-1,3-propanediyl-bis(oxy)]-5-hydroxy-9H-benzo [10,9,11]-5α-estr-15-en-17-one According to general instruction 4b), 920 mg of the compound described under 23a) is reacted with 470 mg of palladium (II) acetate in acetonitrile. After purification, 630 mg of 23b) is obtained.

$^1$H-NMR (CDCl$_3$): δ=7.55 ppm dbr (J=6 Hz,1H,H-15); 6.02 dd (J=6.3 Hz,1H,H-16); 5.48 m (1H,Bridge/11-exo); 4.42 s (1H,OH); 3.50–3.60 m (4H,ketal); 1.04 s (3H,C-18); 1.00 s (3H,Me-ketal); 0.97 s (3H,Me-ketal)

c)   5',6'-Dihydro-3,3-[2,2-dimethyl-1,3-propanediyl-bis(oxy)]-17α-(1-propinyl)-9H-benzo [10,9,11]-5α-estr-15-ene-5,17β-diol According to general instruction 2), 630 mg of 23b) is reacted with 10 ml of a 1.6 molar solution of n-butyllithium as well as propine gas in absolute tetrahydrofuran. The crude product (685 mg) is used without purification in the next stage.

d)   5',6'-Dihydro-17β-hydroxy-17α-(1-propinyl)-9H-benzo[10,9,11]estra-4,15-dien-3-one According to general instruction 1), 685 mg of 23b) is reacted with 4 n hydrochloric acid in acetone. After purification, 430 mg of 23d) is obtained.

$[\alpha]_D^{20}$=−128.7 (CHCl$_3$; c=0.515)

$^1$H-NMR (CDCl$_3$): δ=5.97 ppm dbr (J=6 Hz, 1H, H-15); 5.78 sbr (1H,H-4); 5.73 dd (J=6.3 Hz,1H,H-16); 5.40 m (1H,Bridge/11-exo); 1.90 s (3H,propine); 0.90 s (3H,C-18)

Example 24

17-[Acetyloxy)-5',6'-dihydro-9H-benzo[10,9,11]-19-norpregn-4-ene-3,20-dione a)   5',6'-Dihydro-5,17α-dihydroxy-3,3-[2,2-dimethyl-1,3-propanediylbis(oxy)]-9H-benzo[10,9,11]-5α-estrane-17β-carbonitrile Analogously to example 13a), 1.3 g of 24a) is obtained from 1.6 g of the compound described under 22a), 8 ml of 2-hydroxy-2-methylpropanenitrile and 0.15 ml of 20% aqueous sodium hydroxide solution.

$^1$H-NMR (CDCl$_3$): δ=5.38 ppm m (1H,Bridge/11-exo); 4.50 s (1H,OH); 3.50–3.60 m (4H,ketal); 1.00 s (3H,Me-ketal); 0.98 s (3H,Me-ketal); 0.90 s (3H,C-18)

b)   5',6'-Dihydro-17-hydroxy-9H-benzo[10,9,11]-19-norpregn-4-ene-3,20-dione

Analogously to example 13b), 1.3 g of the substance described under 24a) is reacted with 2.8 ml of ethoxyethene and 120 mg of p-toluenesulfonic acid in diethyl ether. The crude product obtained is again dissolved in diethyl ether and reacted with 5 ml of a 1.6 molar solution of methyllithium in diethyl ether. The obtained crude product is acid-cleaved (according to general instruction 1) with 4 n hydrochloric acid in acetone. After recrystallization from diisopropyl ether/methanol, 700 mg of 24b) is obtained.

$^1$H-NMR (CDCl$_3$): δ=5.77 ppm sbr (1H,H-4); 5.32 m (1H,Bridge/11-exo); 2.28 s (3H,acetyl); 0.78 s (3H,C-18)

c)   17-(Acetyloxy)-5',6'-dihydro-9H-benzo[10,9,11]-19-norpregn-4-ene-3,20-dione 700 mg of the compound described under 24b) is reacted analogously to 13c) with 9 ml of glacial acetic acid and 3.5 ml of trifluoroacetic acid anhydride. After purification, 520 mg of 24c) is obtained.

$^1$H-NMR (CDCl$_3$): δ=5.79 ppm sbr (1H,H-4); 5.48 m (1H,Bridge/11-exo); 2.15 s (3H,acetyl); 2.10 s (3H, acetoxy); 0.62 s (3H,C-18)

Example 25

9,11α-Dihydro-17α-ethinyl-17β-hydroxy-6'H-benzo[10,9,11]18a-homoestr-4-en-3-one a)   17β-Hydroxy-18a-homoestr-5(10)-en-3-one A solution of 252 g of oxalic acid dihydrate in 2 l of water is instilled in a suspension of 355 g of 17β-hydroxy-3-methoxy-18a-homoestra-2,5(10)-diene in 4 l of acetone within 15 minutes, then stirred for 3 l hours, then stirred in 3.6 l of water and extracted twice with 2 l of dichloromethane each. The combined organic phases are washed twice with 1.5 l of saturated sodium bicarbonate solution each, dried on sodium sulfate and concentrated by evaporation in a vacuum. After recrystallization from ethyl acetate, 293 g of 25a) is obtained.

Melting point=103°–105° C., $[\alpha]_D^{20}$+155.0° (CHCl$_3$; c=0.505)

$^1$H-NMR (CDCl$_3$): δ=3.78 ppm dd (J=14,7.5 Hz,1H,H-17); 1.00 t (J=7.5 Hz,3H,18a-CH$_3$)

b)   17β-Hydroxy-18a-homoestra-4,9-dien-3-one 443 g of pyridinium hydrobromide perbromide is slowly added to a solution of 290 g of the compound, described under 25a), in 4 l of pyridine under cooling, so that the temperature does not exceed 25° C. Then, it is stirred for 2 hours at 50° C., then cooled in an ice bath, stirred in 4 l of ice-cooled semiconcentrated hydrochloric acid and then extracted once with 4 l and twice with 2 l of dichloromethane each. The combined organic phases are washed with 4 l of ice-cold semiconcentrated hydrochloric acid, dried on sodium sulfate and concentrated by evaporation in a vacuum. After digestion with warm ethyl acetate, 147.5 g of 25b) is obtained. Chromatography of the mother liquor produces another 41.5 g of 25b).

Melting point=136°–138° C., $[\alpha]_D^{20}$=–293.9° (CHCl$_3$; c=0.510)

$^1$H-NMR (CDCl$_3$): δ=5.68 ppm sbr (1H,4-H); 3.77 dd (J=14,7.5 Hz,1H,H-17); 1.08 t (J=7.5 Hz,3H,18a-CH$_3$)

c) 3,3-[2,2-Dimethyl-1,3-propanediylbis(oxy)]-18a-homoestra-5(10),9(11)-dien-17β-ol 180 g of 2,2-dimethylpropane-1,3-diol, 84 g of trimethylorthoformate and 1 g of p-toluenesulfonic acid monohydrate are added to a solution of 189 g of the compound, described under 25b), in 1.8 l of dichloromethane. After 3 hours of stirring, it is diluted with 1 l of dichloromethane, washed with 2 l of saturated sodium bicarbonate solution, the aqueous phase is extracted twice with 400 ml of dichloromethane each, and, after drying on sodium sulfate, the combined organic phases are concentrated by evaporation in a vacuum. The residue is dissolved in 200 ml of dichloromethane, mixed with 900 ml of methanol and 180 g of potassium carbonate and the mixture is refluxed for 1 hour. The mixture is then concentrated by evaporation in a vacuum to the greatest possible extent, mixed with 2 l of water and then extracted with 2 l and also three times with 400 ml of dichloromethane each. After drying the combined organic phases on sodium sulfate and removal of the solvent in a vacuum, 252 g of 25c) is obtained, which is used without purification in the next stage.

$^1$H-NMR (CDCl$_3$): δ=5.55 ppm m (1H,11-H); 3.86 dd (J=14, 7.5 Hz,1H,H-17); 3.40–3.68 m (4H,ketal); 1.07 s (3H,Me-ketal); 0.94 t (J=7.5 Hz,3H,18a-CH$_3$); 0.90 s (3H, Me-ketal)

d) 3,3-[2,2-Dimethyl-1,3-propanediylbis(oxy)]-5,10α-epoxy-18a-homo-5α-estr-9(11)-en-17β-ol 252 g of the compound described under 25c) is dissolved in 1.2 l of dichloromethane and mixed with 59 g of 2-(3-nitrophenyl)-1,1,1-trifluoroethanone and 190 ml of saturated sodium bicarbonate solution. Under cooling in an ice bath, 240 ml of 30% hydrogen peroxide solution is added and the mixture is stirred for 18 hours at T<10° C. Then, 500 ml of saturated sodium thiosulfate solution is carefully instilled, then diluted with 500 ml of water, the phases are separated and the aqueous phase is extracted twice with 500 ml of dichloromethane each. The combined organic phases are washed with 500 ml of saturated sodium chloride solution, twice with 500 ml of 5% sodium hydroxide solution each and again with 500 ml of saturated sodium chloride solution, dried on sodium sulfate and concentrated by evaporation in a vacuum. 250 g of crude 25d) is obtained, which is used without purification in the next stage.

$^1$H-NMR (CDCl$_3$): δ=6.03 ppm m (1H,11-H); 3.82 m (1H,H-17); 3.36–3.63 m (4H,ketal); 1.07 s (3H,Me-ketal); 0.98 t (J=7.5 Hz,3H,18a-CH$_3$); 0.87 s (3H,Me-ketal)

e) 3,3-[2,2-Dimethyl-1,3-propanediylbis(oxy) ]-19-ethinyl-18a-homo-5α-androst-9 (11)-ene-5,17β-diol 50 g of the compound described under 25d) is reacted analogously to 1a) with Grignard reagent produced from 3-bromopropine. After aqueous working up (F) and purification of the crude product, 33.6 g of 25e) is obtained.

Melting point=112°–114° C., $[\alpha]_D^{20}$=–16.2° (CHCl$_3$; c=0.510)

$^1$H-NMR (CDCl$_3$): δ=5.42 ppm m (1H,H-11); 4.38 s (1H,OH); 3.82 m (1H,H-17); 3.42–3.60 m (4H,ketal); 1.88 t (J=1.5 Hz,1H,ethine); 0.99 s (3H,Me-ketal); 0.92 s (3H, Me-ketal); 0.92 t (J=7.5hz,3H,18a-CH$_3$)

f) 19-(Bromoethinyl)-3,3-[2,2-dimethyl-1,3-propanediyl-bis(oxy)]-18a-homo-5α-androst-9(11)-ene-5,17β-diol 75.5 g of the substance described under 25e) is reacted analogously to 1b) in 2 l of acetone with 2.99 g of silver nitrate and 32.9 g of N-bromosuccinimide. Aqueous working up (B, F) produces 96 g of 25f), which is used without purification in the next stage.

g) 19-(2-Bromoethenyl)-3,3-[2,2-dimethyl-1,3-propanediylbis(oxy)]-18a-homo-5α-androst-9 (11)-ene-5,17β-diol 96 g of the substance described under 25f) is reacted analogously to 1c) in 1.8 l of a mixture of tetrahydrofuran and water (1:1) with 131 g of p-toluenesulfonic acid hydrazide and 87 g of sodium acetate. Aqueous working up (B, F) as well as purification produces 66.7 g of 25g) as light yellow foam.

$[\alpha]_D^{20}$=–157.2° (CHCl$_3$; c=0.515)

$^1$H-NMR (CDCl$_3$): δ=6.15 ppm m (1H,vinyl); 5.78 m (1H,vinyl); 5.34 m (1H,H-11); 4.40 s (1H,OH); 3.83 dd (J=14,7.5 Hz,1H,H-17); 3.46–3.58 m (4H,ketal); 0.98 s (3H,Me-ketal); 0.96 s (3H,Me-ketal); 0.94 t (J=7.5 Hz, 3H, 18a-CH$_3$)

h) 9,11α-Dihydro-3,3-[2,2-dimethyl-1,3-propanediyl-bis(oxy)]-6'H-benzo [10,9,11]-18a-homo-5α-estrane-5,17β-diol 66.3 g of the substance described under 25g) is reacted analogously to 1d) in 1.3 l of toluene with 40 ml of tributyltin hydride and 75 mg of azobis isobutyronitrile. After purification of the crude product, 31 g of 25h) is obtained.

Melting point=213°–215° C., $[\alpha]_D^{20}$=–45.1° (CHCl$_3$; c=0.505)

$^1$H-NMR (CDCl$_3$): δ=5.70 ppm dbr (J=10 Hz,1H,Bridge); 5.48 m (1H,Bridge); 4.37 s (1H,OH); 3.70 m (1H,17-H); 3.48–3.63 m (4H,ketal); 1.07 t (J=7.5 Hz,3H,18a-CH$_3$); 0.99 s (3H,Me-ketal); 0.97 s (3H,Me-ketal)

i) 9,11α-Dihydro-3,3-[2,2-dimethyl-1,3-propanediyl-bis(oxy)]-5-hydroxy-6'H-benzo [10,9,11]-18a-homo-5α-estran-17-one According to general instruction 3), 11.0 g of 25i) is obtained as white crystals from 12.0 g of the substance described under 25h), 16.7 g of chromium trioxide and 57 ml of pyridine in 500 ml of dichloromethane.

Melting point=200°–203° C., $[\alpha]_D^{20}$=–17.4° (CHCl$_3$;c=0.510)

$^1$H-NMR (CDCl$_3$): δ=5.61 ppm dbr (J=10 Hz, 1H,Bridge); 5.52 m (1H,Bridge); 4.40 s (1H,OH); 3.48–3.63 m (4H,ketal); 2.51 m (1H,H-11); 0.99 s (3H,Me-ketal); 0.97 s (3H,Me-ketal); 0.79 t (J=7.5 Hz, 3H, 18a-CH$_3$)

j ) 9,11α-Dihydro-3,3-[2,2-dimethyl-1,3-propanediyl-bis(oxy)]-17α-ethinyl-6'H-benzo [10,9,11]-18a-homo-α-estrane-5,17β-diol According to general instruction 2), 750 mg of the substance described under 25i) and 11 ml of a 1.6 molar solution of n-butyllithium in hexane as well as ethine gas in absolute tetrahydrofuran are reacted. After purification, 620 mg of 25j) is obtained as white crystals.

Melting point=124° C., $[\alpha]_D^{20}$=–49.6° (CHCl$_3$; c=0.520)

$^1$H-NMR (CDCl$_3$): δ=5.72 ppm dbr (J=10 Hz, 1H,Bridge); 5.49 m (1H,Bridge); 4.40 s (1H,OH); 3.50–3.65 m (4H,ketal); 2.60 s (1H,ethine); 2.50 m (1H,H-11); 1.06 t (J=7.5 Hz,3H,18a-CH$_3$); 0.98 s (6H,Me-ketal)

k) 9,11α-Dihydro-17α-ethinyl-17β-hydroxy-6'H-benzo [10,9,11]-18a-homoestr-4-en-3-one According to general instruction 1), 600 mg of 25j) is reacted with 1.5 ml of 4 n hydrochloric acid in acetone. After purification of the crude product, 348 mg of 25k) is obtained as white crystals.

Melting point=242°–245° C., $[\alpha]_D^{20}$=–60.3° (CHCl$_3$; c=0.520)

$^1$H-NMR (CDCl$_3$): δ=5.81 ppm sbr (1H,H-4); 5.77 dbr (J=10 Hz,1H,Bridge); 5.58 m (1H,Bridge); 2.67 m (1H,H-11); 2.62 s (1H,ethine); 1.08 t (J=7.5 Hz,3H,18a-CH$_3$)

Example 26

9,11α-Dihydro-17β-hydroxy-17α-(1-propinyl)-6'H-benzo [10,9,11]-18 a-homoestr-4-en-3-one a) 9,11αDihydro-3,3-[2,2-dimethyl-1,3-propanediyl-bis(oxy)]-17α-(1-propinyl)-6'H-benzo [10,9,11]-18a-homo-5α-estrane-5,17β-diol According to general instruction 2), 750 mg of the compound described under 25i) and 11 ml of a 1.6 molar solution of n-butyllithium in hexane as well as propine gas in absolute tetrahydrofuran are reacted. 705 mg of 26a) is obtained as amorphous solid.

$[\alpha]_D^{20}$=–42.4° (CHCl$_3$; c=0.972)

$^1$H-NMR (CDCl$_3$): δ=5.71 ppm dbr (J=10 Hz,1H,Bridge); 5.48 m (1H,Bridge); 4.46 s (1H,OH); 3.50–3.63 m (4H, ketal); 2.50 m (1H,H-11); 1.88 s (3H,propine) 1.06 t (J=7.5 Hz,3H,18a-CH$_3$); 0.98 s (3H,Me-ketal); 0.96 s (3H,Me-ketal)

b) 9,11αDihydro-17β-hydroxy-17α-(1-propinyl)-6'H-benzo [10,9,11]-18a-homoestr-4-en-3-one According to general instruction 1), 690 mg of the substance described under 26a) is reacted with 2 ml of 4 n aqueous hydrochloric acid in acetone. After purification of the crude product, 380 mg of 26b) is obtained as white crystals.

Melting point=201°–203° C.; $[\alpha]_D^{20}$=–57.4° (CHCl$_3$;c=0.510)

$^1$H-NMR (CDCl$_3$): δ=5.81 ppm sbr (1H,H-4); 5.76 dbr (J=10 Hz,1H,Bridge); 5.56 m (1H,Bridge); 2.68 m (1H,H-11); 1.87 s (3H,propine); 1.07 t (J=7.5 Hz,3H,18a-CH$_3$)

Example 27

9,11α-Dihydro-17α-(1-butinyl)-17β-hydroxy-6'H-benzo [10,9,11]-18 a-homoestr-4-en-3-one a) 9, 11α-Dihydro-3,3-[2,2-dimethyl-1,3-propanediyl-bis(oxy)]-17α-butinyl-6'H-benzo [10,9,11]-18a-homo-5α-estrane-5,17β-diol According to general instruction 2), 800 mg of the compound described under 25 i) and 15 ml of a 1.6 molar solution of n-butyllithium in hexane as well as 5 g of 1-butine in absolute tetrahydrofuran are reacted. 545 mg of 27a) is obtained as white crystals.

Melting point=186°–191° C; $[\alpha]_D^{20}$=–51.2° (CHCl$_3$; c=0.500)

$^1$H-NMR (CDCl$_3$): δ=5.7 ppm dbr (J=10 Hz, 1H,Bridge); 5.48 m (1H,Bridge); 4.42 s (1H,OH); 3.46–3.62 m (4H, ketal); 2.48 m (1H,H 11); 2.23 q (J=7.5 Hz,2H,butine-CH$_2$); 1.12 t (J=7.5 Hz,3H,butine-CH$_3$); 1.06 t (J=7.5 Hz,3H,18a-CH$_3$); 0.98 s (3H,Me ketal); 0.96 s (3H,Me-ketal)

b) 9,11α-Dihydro-17α-(1-butinyl)-17β-hydroxy-6'H-benzo [10,9,11]-18a-homoestr-4-en-3-one According to general instruction 1), 485 mg of the substance described under 27a) is reacted with 1 ml of 4 n aqueous hydrochloric acid in acetone. After purification of the crude product, 323 mg of 27b) is obtained as white crystals.

Melting point=143°–146° C; $[\alpha]_D^{20}$=52.5° (CHCl$_3$; c=0.500)

$^1$H-NMR (CDCl$_3$): δ=5.81 ppm sbr (1H,H-4); 5.77 (dbr (J=10 Hz,1H,Bridge); 5.56 m (1H,Bridge); 2.68 m (1H,H-11); 2.23 q (J=7.5 Hz, 2H, butine -CH$_2$); 1.12 t (J=7.5 Hz, 3H, butine-CH$_3$); 1.07 t (J=7.5 Hz, 3H, 18a-CH$_3$)

Example 28

9,11α-Dihydro-17β-ethenyl-17β-hydroxy-6'H-benzo[10,9,11]-18a-homoestr-4-en-3-one a) 9,11α-Dihydro-3,3-[2,2-dimethyl-1,3-propanediyl-bis(oxy)]-17α-ethenyl-6'H-benzo[10,9,11]-1 8a-homo-5α-estrane-5,17β-diol 14.5 ml of a 1.6 molar solution of n-butyllithium in hexane is instilled at 0° C. in a solution of 1.32 g of tetravinyltin in 50 ml of diethyl ether and stirred for one more hour at room temperature. Then, a solution of 1 g of the compound, described under 25i), in 25 ml of tetrahydrofuran is added. It is allowed to stir for one more hour at 0° C. and then aqueously worked up (C, F). After purification of the crude product, 660 mg of 28a) is obtained as white crystals.

Melting point=117°–121° C.; $[\alpha]_D^{20}$=–37.8° (CHCl$_3$; c=0.520)

$^1$H-NMR (CDCl$_3$): δ=6.08 ppm dd (J=17.5,10 Hz,1H, vinyl); 5.7 dbr (J=10 Hz,1H,Bridge); 5.46 m° (1H,Bridge); 5.12 dd (J=17.5,2 Hz,1H,vinyl); 5.07 dd (J=10.2 Hz,1H, vinyl); 4.38 s (1H,OH); 3.48–3.60 m (4H,ketal); 2.42 m (1H,H-11); 1.09 t (J=7.5 Hz,3H,18a-CH$_3$); 0.98 s (6H,Me-ketal)

b) 9,11α-Dihydro-17α-ethenyl-17β-hydroxy-6'H-benzo [10,9,11]-18a-homoestr-4-en-3-one According to general instruction 1), 600 mg of the substance described under 28a) is reacted with 1.3 ml of 4 n aqueous hydrochloric acid in acetone. After purification of the crude product, 406 mg of 28b) is obtained as white crystals.

Melting point=170°–173° C.; $[\alpha]_D^{20}$=24.4° (CHCl$_3$; c=0.515)

$^1$H-NMR (CDCl$_3$): δ=6.06 ppm dd (J=17.5,10 Hz, 1H, vinyl); 5.80 sbr (1H,H-4); 5.75 dbr (J=10 Hz,1H,Bridge); 5.56 m (1H,Bridge); 5.12 dd (J=17.5,2 Hz, 1H, vinyl); 5.08 dd (J=10.2 Hz, 1H,vinyl); 1.12 t (J=7.5 Hz, 3H, 18a-CH$_3$)

9,11α-Dihydro-17β-hydroxy-17α-(trifluoromethyl)-6'H-benzo[10,9,11-18a-homoestr-4-en-3-one a) 9,11α-Dihydro-3,3-[2,2-dimethyl-1,3-propanediyl-bis(oxy)]-17α-(trifluoromethyl)-5-(trimethylsilyloxy)-6'H-benzo[10,9,11]-18a-homo-5α-estran-17β-ol 1.7 ml of trifluoromethyl trimethylsilane and then 2.8 ml of a one-molar solution of tetra-n-butylammonium fluoride in tetrahydrofuran are instilled in a solution of 1 g of the compound, described under 25i), in 15 ml of tetrahydrofuran at –10° C. It is stirred for 30 more minutes, then poured on a mixture of ethyl acetate and water, the aqueous phase is extracted twice with ethyl acetate, the combined organic phases are dried on sodium sulfate and concentrated by evaporation in a vacuum. 1.39 g of 29a) is obtained as white foam, which is used without purification in the next stage.

$^1$H-NMR (CDCl$_3$): δ=5.70 ppm dbr (J=10 Hz, 1H,Bridge); 5.50 m (1H,Bridge); 3.63 m (2H,ketal); 3.30 m (2H,ketal); 2.50 m (1H,H-11); 1.16 s (3H,Me-ketal); 1.04 t (J=7.5 Hz, 3H, 18a-CH$_3$); 0.77 (3H,Me-ketal); 0.14 s (9H, Me$_3$Si)

b) 9,11α-Dihydro-17β-hydroxy-17α-(trifluoromethyl)-6'H-benzo[10,9,11]-18a-homoestr-4-en-3-one According to general instruction 1), 1.38 g of the substance described under 29a) is reacted with 2.8 ml of 4 n aqueous hydrochloric acid in acetone. After purification of the crude product, 302 mg of 29b) is obtained as white foam.

$[\alpha]_D^{20}$=−17.6° (CHCl$_3$;c=0.505)

$^1$H-NMR (CDCl$_3$): δ=5.80 ppm sbr (1H,H-4); 5.77 dbr (J=10 Hz,1H,Bridge); 5.58 m (1H,Bridge); 2.67 m (1H,H-11); 1.08 t (J=7.5 Hz, 3H, 18a-CH$_3$)

Example 30

9,11α-Dihydro-17α-(cyanomethyl)-17β-hydroxy-6'H-benzo[10,9,11]-18a-homoestr-4-en-3-one a) 9,11α-Dihydro-3,3-[2,2-dimethyl-1,3-propanediyl-bis(oxy)]-17α-(cyanomethyl)-6'H-benzo[10,9,11]-18a-homo-5α-estrane-5,17β-diol 0.82 g of acetonitrile is instilled in a solution of lithium diisopropylamide produced according to general instruction 4a) from 2.8 ml of diisopropylamine and 12.5 ml of a 1.6 molar solution of n-butyllithium at −70° C., allowed to stir for 30 more minutes at −70° C. and then a solution of 1.29 g of the substance, described under 25i), in 10 ml of tetrahydrofuran is added and allowed to warm within four hours to −40° C. After aqueous working up (C, F) and purification, 1.06 g of 30a) is obtained.

$^1$H-NMR (CDCl$_3$): δ=5.70 ppm dbr (J=10 Hz,1H,Bridge); 5.49 m (1H,Bridge); 4.40 s (1H,OH); 3.47–3.65 m (4H, ketal); 2.65 and 2.52 Aβ-signal (J$_{AB}$=15 Hz,2H,CH$_2$CN); 2.50 m (1H,H-11); 1.06 t (J=7.5 Hz,3H,18a-CH$_3$); 0.98 s (6H,Me-ketal)

b) 9,11α-Dihydro-17α-(cyanomethyl)-17β-hydroxy-6'H-benzo[10,9,11]-18a-homoestr-4-en-3-one According to general instruction 1), 1.04 g of the substance described under 30a) is reacted with 1.1 ml of 4 n aqueous hydrochloric acid in acetone. After purification of the crude product, 640 mg of 28b) is obtained as white crystals.

Melting point=207°–212° C.

$^1$H-NMR (CDCl$_3$): δ=5.80 ppm sbr (1H,H-4); 5.76 dbr (J=10 Hz,1H,Bridge); 5.59 m (1H,Bridge); 2.67 and 2.52 Aβ-signal (J$_{AB}$=15 Hz,2H,CH$_2$CN); 1.10 t (J=7.5 Hz,3H, 18a-CH$_3$)

Example 31

9,11α-Dihydro-17β-hydroxy-17α-(1,2-propadienyl)-6'H-benzo[10,9,11]-18a-homoestr-4-en-3-one a) 9,11α-Dihydro-3,3-[2,2-dimethyl-1,3-propanediyl-bis(oxy)]-17α-[3-[(tetrahydro-2H-pyran-2-yl)oxy]-1-propinyl]-6'H-benzo[10,9,11]-18a-homo-5α-estrane-5,17β-diol The lithium-organic compound is produced from 10.7 ml of 3-[(tetrahydro-2H-pyran-2-yl)oxy]-1-propine in 380 ml of absolute tetrahydrofuran and 48 ml of a 1.6 molar solution of n-butyllithium in hexane at 0° C. under argon. Then, a solution of 3.3 g of the substance, described under 25i), in 80 ml of absolute tetrahydrofuran is added. It is allowed to stir for one more hour at 0° C. and then aqueously worked up (C, F). After purification, 3.7 g of 31a) is obtained as white foam.

$[\alpha]_D^{20}$=−39.4° (CHCl$_3$; c=0.545)

$^1$H-NMR (CDCl$_3$): δ=5.70 ppm dbr (J=10 Hz, 1H,Bridge); 5.48 m (1H,Bridge); 4.82 m (1H,THP); 4.39 s (1H,OH); 4.32 m (2H,CH$_2$OTHP); 3.87 m (1H,THP); 3.47–3.63 m (5H,ketal and THP); 2.48 m (1H,H-11); 1.02 t (J=7.5 Hz,3H,18a-CH$_3$); 0.95 m (6H,Me-ketal)

b) 9,11α-Dihydro-3,3-[2,2-dimethyl-1,3-propanediyl-bis(oxy)]-17α-(1,2-propadienyl)-6'H-benzo[10,9,11]-18a-homo-5α-estrane-5,17β-diol A solution of 1.1 g of the compound, described under 31a), in 25 ml of diethyl ether is instilled in 30 ml of a one-molar solution of lithium aluminum hydride in tetrahydrofuran and refluxed for six hours. Then, 10 ml of acetone and then 50 ml of saturated sodium sulfate solution are instilled under ice cooling, the solids are suctioned off, rewashed with dichloromethane, the combined organic phases are dried on sodium sulfate, concentrated by evaporation in a vacuum and the remaining resin is purified column-chromatographically on silica gel with a mixture of hexane/ethyl acetate. 230 mg of 31b) is obtained as white foam.

$^1$H-NMR (CDCl$_3$): δ=5.71 ppm dbr (J=10 Hz, 1H,Bridge); 5.48 m (1H,Bridge); 5.42 dd (J=7.7 Hz, 1H, allene); 4.88 m (2H, allene); 4.40 s (1H,OH); 3.48–3.63 m (4H,ketal); 2.46 m (1H,H-11); 1.08 t (J=7.5 Hz,3H,18a-CH$_3$); 0.98 s (6H,Me-ketal)

c) 9,11α-Dihydro-17β-hydroxy-17α-(1,2-propadienyl)-6'H-benzo [10,9,11]-18a-homo-estr-4-en-3-one 180 mg of the substance described under 31b) is reacted according to general instruction 1) in acetone with 0.38 ml of 4 n aqueous hydrochloric acid. After purification of the crude product, 135 mg of 31c) is obtained as white foam.

$^1$H-NMR (CDCl$_3$): δ=5.80 ppm sbr (1H,H-4); 5.77 dbr (J=10 Hz,1H,Bridge); 5.57 m (1H,Bridge); 5.41 dd (J=7.7 Hz, 1H, allene); 4.90 d (J=7 Hz, 2H, allene); 2.54 m (1H,H-11); 1.12 t (J=7.5 Hz,3H,18a-CH$_3$)

Example 32

9,11α-Dihydro-17β-hydroxy-17α-(3methyl-1,2-butadienyl)-6'H-benzo[10,9,11]-18a-homoestr-4-en-3-one a) 9,11α-Dihydro-3,3-[2,2-dimethyl-1,3-propanediyl-bis(oxy)]-17α-[3-methyl-3-[(tetrahydro-2H-pyran-2-yl)oxy]-1-butinyl]-6'H-benzo[10,9,11]-18a-homo-5α-estrane-5,17β-diol The lithium-organic compound is produced from 19.5 ml of 3-methyl-3-[(tetrahydro-2H-pyran-2-yl) oxy]-1-butine in 570 ml of absolute tetrahydrofuran and 72.5 ml of a 1.6 molar solution of n-butyllithium in hexane at 0° C. under argon. Then, a solution of 5 g of the substance, described under 25i), in 120 ml of absolute tetrahydrofuran is added. It is allowed to stir for 30 more minutes at 0° C. and then aqueously worked up (C, F). After purification, 4.22 g of 32a) is obtained as white foam.

$[\alpha]_D^{20}$=−47.4 (CHCl$_3$; c=0.535)

$^1$H-NMR (CDCl$_3$): δ=5.70 ppm dbr (J=10 Hz, 1H,Bridge); 5.48 m (1H,Bridge); 5.00 m (1H,THP); 4.30 s (1H,OH); 3.96 m (1H,THP); 3.42–3.65 m (5H,ketal and THP); 2.48 m (1H,H-11); 1.52 s (3H,Me); 1.49 s (3H,Me); 1.05 t (J=7.5 Hz, 3H, 18a-CH$_3$); 0.97 s (3H,Me-ketal); 0.95 s (3H,Me-ketal)

b) 9,11α-Dihydro-3,3-[2,2-dimethyl-1,3-propanediyl-bis(oxy)]-17α-(3-methyl-1, 2-butadienyl)-6'H-benzo[10,9,11]-18a-homo-5α-estrane-5,17β-diol A suspension of 3.8 g of lithium aluminum hydride in 70 ml of diethyl ether is refluxed for one hour. Then, a solution of 4 g of the compound, described under 32a), in 100 ml of diethyl ether is instilled at room temperature within 30 minutes and then refluxed for two hours. Then, 40 g of sodium sulfate decahydrate is stirred in the reaction mixture, stirred for one more hour, suctioned off on Celite, rewashed with dichloromethane and the solvent is removed in a vacuum. After purification, 1.2 g of 32b) is obtained as white crystals.

Melting point=15520 C., $[\alpha]_D^{20}$=–54.0° (CHCl$_3$; c=0.525)

$^1$H-NMR (CDCl$_3$): δ=5.72 ppm dbr (J=10 Hz, 1H,Bridge); 5.48 m (1H,Bridge); 5.42 m (1H,allene); 4.38 s (1H,OH); 3.46–3.64 m (4H,ketal); 2.45 m (1H,H-11); 1.75 d (J=2 Hz,3H,Me-allene); 1.74 d (J=2 Hz,3H,Me-allene); 1.08 t (J=7.5 Hz,3H,18a-CH$_3$); 0.99 s (3H,Me-ketal); 0.95 s (3H,Me-ketal)

c) 9,11α-Dihydro-17β-hydroxy-17α-(3-methyl-1,2-butadienyl)-6'H-benzo [10,9,11]-18a-homoestr-4-en-3-one According to general instruction 1), 620 mg of 32b) is reacted with 4 n hydrochloric acid in acetone. After one hour of stirring at room temperature, it is worked up (B, F) and, after purification of the crude product, 177 mg of 36b) is obtained as white crystals.

Melting point=150°–152° C., $[\alpha]_D^{20}$=–68.5° (CHCl$_3$; c=0.460)

$^1$H-NMR (CDCl$_3$): δ=5.78 ppm sbr (1H,H-4); 5.76 dbr (J=10 Hz,1H,Bridge); 5.55 m (1H,Bridge); 5.20 m (1H, allene); 2.52 m (1H,H-11); 1.75 d (J=2.5 Hz,3H,Me-allene); 1.72 d (J=2.5 Hz,3H,Me-allene); 1.12 t (J=7.5 Hz,3H,18a-CH$_3$)

Example 33

5",4",9,11α-Tetrahydrospiro[6'H-benzo[10,9,11]-18a-homoestr-4-ene-17β,2"(5")-furan]-3,5"-dione a) 5",4"9,11α-Tetrahydro-3,3-[2,2-dimethyl-1,3-propanediylbis(oxy)][spiro[5-hydroxy-6'H-benzo[10,9,11]-18a-homo-5α-estrane-17β,2"(5")furan]-5-ol-5"-one A solution of 8.6 ml of allyltetramethylphosphorus diamidate in 40 ml of tetrahydrofuran is instilled in a mixture of 70 ml of tetrahydrofuran and 60 ml of a 1.6 molar solution of n-butyllithium in n-hexane at –50° C. within 20 minutes and stirred for one more hour at –30° C. Then, a solution of 2 g of the compound, described under 25i), in 15 ml of tetrahydrofuran is instilled, allowed to heat to room temperature within one hour and stirred for four more hours. After aqueous working up (C, F) and purification, 995 mg of 33a) is obtained as white foam.

$^1$H-NMR (CDCl$_3$): δ=5.70 ppm dbr (J=10 Hz,1H,Bridge); 5.50 m (1H,Bridge); 4.42 s (1H,OH); 3.48–3.63 m (4H, ketal); 1.03 t (J=7.5 Hz,3H,18a-CH$_3$); 0.98 s (6H,Me-ketal)

b) 5",4",9,11α-Tetrahydrospiro[6'H-benzo[10,9,11]-18a-homoestr-4-ene-17β,2"(5")-furan]-3,5"-dione According to general instruction 1), 818 mg of the substance described under 33a) is reacted with 2.3 ml of 4 n aqueous hydrochloric acid in acetone. After purification of the crude product, 441 mg of 33b) is obtained as white crystals.

Melting point=100°–102° C.; $[\alpha]_D^{20}$+23.75° (CHCl$_3$; c=0.500)

$^1$H-NMR (CDCl$_3$): δ=5.82 ppm sbr (1H,H-4); 5.75 dbr (J=10 Hz,1H,Bridge); 5.58 m (1H, Bridge); 2.68 m (1H, 11-H); 1.05 t (J=7.5 Hz, 3H, 18a-CH$_3$)

Example 34

9,11α-Dihydro-17α-ethinyl-17β-hydroxy-6'H-benzo[10,9,11]-18a-homoestra-4,5-dien-3-one a) 9,11α-Dihydro-3,3-[2,2-dimethyl-1,3-propanediylbis(oxy)]-17-[(trimethylsilyl)oxy]-6'H-benzo [10,9,11]-18a-homo-5α-estr-16-en-5-ol According to general instruction 4a), 2.15 g of the substance described under 25i) is reacted with 2.5 ml of diisopropylamine, 11 ml of a 1.6 molar solution of n-butyllithium in hexane and 3.1 ml of trimethylchlorosilane in absolute tetrahydrofuran. 2.52 g of 34a) is obtained as crude product, which is used without further purification in the next stage.

Melting point=172°–174° C.

$^1$H-NMR (CDCl$_3$): δ=5.58 ppm dbr (J=10 Hz, 1H,Bridge); 5.44 m (1H,Bridge); 4.46 m (1H,H-16); 4.37 s (1H,OH); 3.48–3.64 m (4H,ketal); 2.48 m (1H,H-11); 0.98 s (3H,Me-ketal); 0.96 s (3H,Me-ketal); 0.87 t (J=7.5 Hz, 3H, 18a-CH$_3$); 0.18 s (9H,Me-Si)

b) 9,11α-Dihydro-3,3-[2,2-dimethyl-1,3-propanediylbis(oxy)]-5-hydroxy-6'H-benzo[10,9,11]-18a-homo-5α-estr-15-en-17-one According to general instruction 4b), 2.42 g of the compound described under 34a) is reacted with 1.19 g of palladium(II) acetate in acetonitrile. After purification, 1.34 g of 34b) is obtained as white crystals.

Melting point=210°–212° C.; $[\alpha]_D^{20}$=128.5° (CHCl$_3$; c=0.505)

$^1$H-NMR (CDCl$_3$): δ=7.54 ppm dbr (J=8 Hz,1H,H-15), 5.96 jj (J=6.3 Hz, 1H,H-16); 5.63 dbr (J=10 Hz, 1H,Bridge); 5.52 m (1H,Bridge); 4.47 s (3H,OH); 3.46–3.63 m (4H, ketal); 2.56 m (1H,H-11); 0.98 s (3H,Me-ketal); 0.96 s (3H,Me-ketal); 0.78 t (J=7.5 Hz, 3H, 18a-CH$_3$)

c) 9,11α-Dihydro-3,3-[2,2-dimethyl-1,3-propanediylbis(oxy)]-17α-ethinyl-6'H-benzo [10,9,11]-18a-homo-5α-estr-15-ene-5,17β-diol According to general instruction 2), 1.0 g of 34b), 15 ml of a 1.6 molar solution of n-butyllithium in hexane as well as ethine gas in absolute tetrahydrofuran are reacted. 1.23 g of 34c) is obtained, which is used without purification in the next stage.

$^1$H-NMR (CDCl$_3$): δ=5.97 ppm dbr (J=6 Hz,1H,H-15); 5.63 m (2H,H-16 and Bridge); 5.48 m (1H,Bridge); 4.42 s (1H,OH); 3.50–3.65 m (4H,ketal); 2.62 s (1H,ethine); 2.58 m (1H,H-11); 0.98 s (6H,Me-ketal); 0.82 t (J=7.5 Hz,3H, 18a-CH$_3$)

d) 9,11α-Dihydro-17α-ethinyl-17β-hydroxy-6'H-benzo [10,9,11]-18a-homoestra-4,15-dien-3-one According to general instruction 1), 1.1 g of 34c) is reacted with 4 n hydrochloric acid in acetone. After purification, 620 mg of 34d) is obtained.

Melting point=201°–203° C.; $[\alpha]_D^{20}$=–198.0° (CHCl$_3$; c=0. 510)

$^1$H-NMR (CDCl$_3$): δ=5.97 dbr (J=6 Hz,1H,H-15); 5.82 sbr (1H,H-4); 5.68 dd (J=6.3 Hz,1H,H-16); 5.66 m (1H, Bridge); 5.58 m (1H,Bridge); 2.75 m (1H,H-11); 2.66 s (1H,ethine); 0.86 t (J=7.5 Hz,3H,18a-CH$_3$)

Example 35

9,11α-Dihydro-17β-hydroxy-17α-(1-propinyl)-6'H-benzo [10,9,11]-18a-homoestra-4,15-dien-3-one a) 9,11α-Dihydro-3,3-[2,2-dimethyl-1,3-propanediylbis(oxy)]-17α-(1-propinyl)-6'H-benzo[10,9,11]-18a-homo-5α-estr-15-ene-5,17β-diol According to general instruction 2), 600 mg of 34b), 8.7 ml of a 1.6 molar solution of n-butyllithium in hexane as well as propine gas in absolute tetrahydrofuran are reacted. 715 mg of 35a) is obtained, which is used without purification in the next stage.

$^1$H-NMR (CDCl$_3$): δ=5.90 ppm dbr (J=6 Hz,1H,H-15); 5.62 m (2H,H-16 and Bridge); 5.48 m (1H,Bridge); 4.46 s (1H,OH); 3.48–3.63 m (4H,ketal); 2.56 m (1H,H-11); 1.90 s (3H,propine); 0.98 s (3H,Me-ketal); 0.97 s (3H,Me-ketal); 0.82 t (J=7.5 Hz,3H,18a-CH$_3$)

b) 9,11α-Dihydro-5,17β-dihydroxy-17α-(1-propinyl)-6'H-benzo[10,9,11]-18a-homo-5α-estr-15-en-3-one 542 mg of the compound described under 35a) is dissolved in 10 ml of acetone, mixed with 1.2 ml of 0.5n hydrochloric acid and stirred for 2.5 hours at room temperature. It is poured on saturated sodium bicarbonate solution, extracted three times with dichloromethane and the combined organic phases are dried on sodium sulfate. After removal of the solvent, 438 mg of 35b) is obtained, which is used without purification in the next stage.

$^1$H-NMR (CDCl$_3$): δ=5.90 dbr (J=6 Hz,1H,H-15); 5.72 dbr (J=10 Hz,1H,Bridge); 5.65 dd (J=6.3 Hz,1H,H-16); 5.56 m (1H,Bridge); 2.64 m (1H,H-11); 1.92 s (3H,propine); 0.85 t (J=7.5 Hz, 3H, 18a-CH$_3$)

c) 9,11α-Dihydro-17β-hydroxy-17α-(1-propinyl)-6'H-benzo [10,9,11]-18a-homoestra-4,15-dien-3-one 400 mg of the compound described under 35b) is dissolved in 10 ml of acetone, mixed with 0.5 ml of 4 n hydrochloric acid and stirred for 5 hours at room temperature. After aqueous working up (B, F) and purification, 139 mg of 35c) is obtained as white crystals.

Melting point=68°–73° C; $[α]_D^{20}$=−53.2° (CHCl$_3$; c=0.500)

$^1$H-NMR (CDCl$_3$): δ=5.90 dbr (J=6 Hz,1H,H-15); 5.83 sbr (1H,H-4); 5.68 m (1H,Bridge); 5.66 m (1H,H-16); 5.58 m (1H,Bridge); 2.72 m (1H,H-11); 1.90 s (3H,propine); 0.86 t (J=7.5 Hz, 3H, 18a-CH$_3$)

Example 36

17α-(1-Butinyl)-9,11α-dihydro-17β-hydroxy-6'H-benzo10, 9,11]- 18a-homoestra-4,15-dien-3-one a) 17α-(1-Butinyl)-9,11α-dihydro-3,3-[2,2-dimethyl-1,3-propanediylbis(oxy)]-6'H-benzo-[10,9,11]-18a-homo-5α-estr-15-ene-5,17β-diol According to general instruction 2), 800 mg of 34b), 15 ml of a 1.6 molar solution of n-butyllithium in hexane as well as 5 g of 1-butine in absolute tetrahydrofuran are reacted. After purification, 637 mg of 36a) is obtained as white foam.

$^1$H-NMR (CDCl$_3$): δ=5.90 ppm dbr (J=6 Hz,1H,H-15); 5.63 m (2H,H-16 and Bridge); 5.48 m (1H,Bridge); 4.43 s (1H,OH); 3.46–3.63 m (4H,ketal); 2.25 q (J=7.5 Hz,2H, butine-CH$_2$); 1.16 t (J=7.5 Hz,3H,butine-CH$_3$); 0.98 s (3H, Me-ketal); 0.96 s (3H,Me-ketal); 0.81 t (J=7.5 Hz,3H,18a-CH$_2$)

b) 17α-(1-Butinyl)-9,11α-dihydro-17β-hydroxy-6'H-benzo [10,9,11]-18a-homoestra-4,15-dien-3-one According to general instruction 1), 364 mg of 36a) is reacted with 4 n hydrochloric acid in acetone. After three hours of stirring at room temperature, it is worked up (B, F) and after purification of the crude product, 145 mg of 36b) is obtained as white foam.

$[α]_D^{20}$=−195.2 (CHCl$_3$; c=0.500)

$^1$H-NMR (CDCl$_3$): δ=5.87 dbr (J=6 Hz,1H,H-15); 5.82 sbr (1H,H-4); 5.68 m (2H,H-16 and Bridge); 5.56 m (1H, Bridge); 2.72 m (1H,H-11); 2.26 q (J=7.5 Hz,2H,butine-CH$_2$); 1.14 t (J=7.5 Hz, 3H, butine-CH$_3$); 0.85 t (J=7.5 Hz, 3H, 18a-CH$_3$)

Example 37

9,11α-Dihydro-17β-hydroxy-17α-(1,3-pentadiinyl)-6'H-benzo[10,9,11]-18a-homoestra-4,15-dien-3-one 300 mg of the substance described under 34d) is dissolved in 40 ml of triethylamine. The solution is saturated at room temperature with propine gas, 90 mg of tetrakis(triphenylphosphine)palladium and 45 mg of copper(I) iodide are added, heated to 60° C. and, while maintaining the propine stream, allowed to stir for one more hour at this temperature. Then, the reaction solution is filtered on Celite and concentrated by evaporation in a vacuum. After purification, 66 mg of 37) is obtained as amorphous solid.

$^1$H-NMR (CDCl$_3$): δ=5.95 dbr (J=6 Hz,1H,H-15); 5.82 sbr (1H,H-4); 5.68 m (1H,Bridge); 5.63 dd (J=6.3 Hz,1H, H-16); 5.56 m (1H,Bridge); 2.74 m (1H,H-11); 1.96 s (3H,pentadiine-Me); 0.82 t (J=7.5 Hz, 3H, 18a-CH$_3$)

Example 38

9,11α,15α,16α-Tetrahydro-17α-ethinyl-17β-hydroxy-6'H-benzo[10,9,11][3"H]cyclopropa[15,16-18a-homoestr-4-en-3-one a) 9,11α,15α,16α-Tetrahydro-3,3-[2,2-dimethyl-1,3-propanediylbis(oxy)]-5-hydroxy-6'H-benzo[10,9,11][3"H]cyclopropa[15,16]-18a-homo-5α-estran-17-one 430 mg of sodium hydride is added to a suspension of 3.68 g of trimethylsulfoxonium iodide in 50 ml of dimethyl sulfoxide, stirred for 90 minutes, then 2 g of the substance described under 34b) is added and allowed to stir for six hours. The mixture is stirred in ice water; the precipitated material is suctioned off, taken up in dichloromethane, dried on sodium sulfate and the solvent is removed in a vacuum. 1.67 g of 38a) is obtained as white crystals.

Melting point=226°–230° C., $[α]_D^{20}$=−70.0° (CHCl$_3$; c=0.500)

$^1$H-NMR (CDCl$_3$): δ=5.56 ppm dbr (J=10 Hz, 1H,Bridge); 5.48 m (1H,Bridge); 4.45 s (1H,OH); 3.46–3.64 m (4H,ketal); 2.54 s (1H,H-11); 1.00 s (3H,Me-ketal); 0.97 s (3H,Me-ketal); 0.76 t (J=7.5 Hz, 3H, 18a-CH$_3$)

b) 9,11α,15α,16α-Tetrahydro-3,3-[2,2-dimethyl-1,3-propanediylbis(oxy)]-17α-ethinyl-6'H -benzo[10,9,11][3"H] cyclopropa[15,16]-18a-homo-5α-estrane-5,17β-diol According to general instruction 2), 1.0 g of the substance described under 38a) and 14 ml of 1.6 molar solution of n-butyllithium in hexane as well as ethine gas in absolute tetrahydrofuran are reacted. After purification, 949 mg of 38b) is obtained as white crystals.

Melting point=197°–202° C., $[α]_D^{20}$=−86.8 (CHCl$_3$; c=0.530)

$^1$H-NMR (CDCl$_3$): δ=5.72 ppm dbr (J=10 Hz, 1H,Bridge); 5.47 m (1H,Bridge); 4.40 s (1H,OH); 3.48–3.65 m (4H,ketal); 2.70 s (1H,ethine); 2.50 m (1H,H-11); 0.99 t (J=7.5 Hz,3H,18a-CH$_3$); 0.97 s (6H,Me-ketal); 0.81 m (1H, cyclopropyl-H)

c) 9,11α,15α,16α-Tetrahydro-17α-ethinyl-17β-hydroxy-6'H-benzo[10,9,11][3"H]cyclopropa[15,16]-18a-homoestr-4-en-3-one According to general instruction 1), 650 mg of 38b) is reacted with 4 n hydrochloric acid in acetone. After purification, 348 mg of 38c) is obtained.

Melting point=227°–230° C; $[α]_D^{20}$=−82.9° (CHCl$_3$; c=0.505)

$^1$H-NMR (CDCl$_3$): δ=5.83 sbr (1H,H-4); 5.78 dbr (J=10 Hz,1H,Bridge); 5.56 m (1H,Bridge); 2.72 s (1H,ethine); 1.02 t (J=7.5 Hz,3H,18a-CH$_3$); 0.48 m (1H,cyclopropyl-H)

Example 39

17-(Acetyloxy)-9,11α-dihydro-6'H-benzo[10,9,11]-18a-homo-19-norpregn-4-ene-3,20-dione a) [17(21)S]-21-phenylsulfinyl)-9,11α-dihydro-3,3-[2,2-dimethyl-1,3-propanediylbis(oxy)]-5-hydroxy-6'H-benzo [10,9,11]-18a-homo-19-nor-5α-pregna-17(20),20-diene A solution of 285 mg of phenylsulfenyl chloride in 0.7 ml of dichloromethane is instilled in a solution of 500 mg of the substance, described under 25i), in 7 ml of dichloromethane and 1 ml of triethylamine at −70° C., then allowed to heat to −30° C. and stirred for three hours at −30° C. The reaction mixture is mixed with water, extracted twice with ethyl acetate, the combined organic phases are washed with 1n aqueous hydrochloric acid and water, dried on sodium sulfate and concentrated by evaporation in a vacuum. After purification, 445 mg of 39a) is obtained.

$^1$H-NMR (CDCl$_3$): δ=7.68 ppm m (2H, aromatic hydrocarbon); 7.50 m (3H, aromatic hydrocarbon); 6.06 t (J=3.5 Hz, 1H, allene); 5.60 dbr (J=10 Hz,1H,Bridge); 5.50 m (1H,Bridge); 4.37 s (1H,OH); 3.48–3.63 m (4H,ketal); 0.97 s (3H,Me-ketal); 0.95 s (3H,Me-ketal); 0.93 t (J=7.5 Hz, 3H, 18a-CH$_3$)

b)  9,11α-Dihydro-3,3-[2,2-dimethyl-1,3-propanediyl-bis(oxy)]-5,17-dihydroxy-20-(methyloxy)-6'H-benzo [10,9,11]-18a-homo-19-nor-5α-pregn-20-ene 24 ml of a 1 molar solution of sodium methanolate in methanol is instilled in a solution of 3.3 g of the compound, described under 39a), in 30 ml of tetrahydrofuran, allowed to stir for 48 hours at room temperature, then poured on water, extracted three times with dichloromethane, the combined organic phases are dried on sodium sulfate, filtered, and the solvent is removed in a vacuum. The residue is dissolved in 65 ml of methanol, 10 ml of triethyl phosphite is added, refluxed for 45 minutes and then concentrated by evaporation in a vacuum. After purification, 2.1 g of 39b) is obtained.

$^1$H-NMR (CDCl$_3$): δ=5.67 ppm dbr (J=10 Hz,1H,Bridge); 5.43 m (1H,Bridge); 4.30 d (J=4 Hz,1H,H-21); 4.30 s (1H,OH); 3.98 d (J=4 Hz,1H,H-21); 3.52 s (3H,MeO); 3.45–3.64 m (4H,ketal); 0.97 s (3H,Me-ketal); 0.95 s (3H, Me-ketal); 0.72 t (J=7.5 Hz, 3H, 18a-CH$_3$)

c)  9,11α-Dihydro-5-hydroxy-6'H-benzo-[10,9,11]-18a-homo-19-nor-5α-pregnane-3,20-dione 2 ml of 4 n aqueous hydrochloric acid is added to a solution of 2.0 g of the compound, described under 39b), in 5 ml of acetone, stirred for one hour at room temperature and the precipitated substance is suctioned off. 1.31 g of 39c) is obtained, which is used without purification in the next stage.

$^1$H-NMR (D6-DMSO): δ=5.76 ppm dbr (J=10 Hz,1H, Bridge); 5.62 m (1H,Bridge); 5.17 s (1H,OH); 4.40 s (1H, OH); 2.25 s (3H,acetyl); 0.70 t (J=7.5 Hz,3H,18a-CH$_3$)

d)  17-(Acetyloxy)-9,11α-dihydro-6'H-benzo[10,9,11]-18a-homo-19-norpregn-4-ene-3,20-dione Analogously to example 13c), 1.3 g of the compound, described under 39c), in 25 ml of glacial acetic acid is reacted with 6.6 ml of trifluoroacetic acid anhydride. After aqueous working up (B, F) and purification, 1.0 g of 39d) is obtained.

Melting point=225°–229° C.

$^1$H-NMR (CDCl$_3$): δ=5.82 ppm sbr (1H,H-4); 5.70 dbr (J=10 Hz,1H,Bridge); 5.58 m (1H,Bridge); 2.72 m (1H,H-11); 2.12 s (3H,acetyl); 2.10 s (3H,acetoxy); 0.72 t (J=7.5 Hz, 3H, 18a-CH$_3$)

Example 40

17-(Acetyloxy)-9,11α-dihydro-β-methylene-6'H-benzo[10,9,11]-18a-homo-19-norpregn-4-ene-3,20-dione 1.41 g of the substance described under 39d) is reacted analogously to the instruction indicated in example 16). 1.03 g of 40) is obtained as white crystals.

Melting point=215°–219° C., [α]$_D^{20}$126.4° (CHCl$_3$; c=0.500)

$^1$H-NMR (CDCl$_3$): δ=6.01 ppm sbr (1H,H-4); 5.70 dbr (J=10 Hz, 1H,Bridge); 5.55 m (1H,Bridge); 5.15 m (1H, exo-methylene); 5.00 m (1H, exo-methylene); 2.74 m (1H, H-11); 2.14 s (3H,acetyl); 2.12 s (3H,acetoxy); 0.72 t (J=7.5 Hz, 3H, 18a-CH$_3$)

Example 41

17-(Acetyloxy)-9,11α-dihydro-β-methyl-6'-H-benzo[10,9,11]-18a-homo-19-norpregna-4,6-diene-3,2-dione 423 mg of the substance described under example 40) is reacted analogously to the instructions indicated in example 18). 303 g of 41) is obtained as white crystals.

Melting point=260°–264° C., [α]$_D^{20}$=+43.4° (CHCl$_3$; c=0.500)

$^1$H-NMR (CDCl$_3$): δ=6.00 ppm sbr (1H,H-7); 5.92 sbr (1H,H-4); 5.72 dbr (J=10 Hz,1H,Bridge); 5.62 m (1H, Bridge); 2.75 m (1H,H-11); 2.15 s (3H,acetyl); 2.11 s (3H,acetoxy); 1.86 sbr (3H, β-methyl); 0.73 t (J=7.5 Hz, 3H, 18a-CH$_3$)

Example 42

5',6'-Dihydro-17β-hydroxy-17α-(1-propinyl)-9H-benzo[10,9,11]-18a-homoestr-4-en-3-one a)  5',6'-Dihydro-3,3-[2,2-dimethyl-1,3-propanediyl-bis(oxy)]-9H-benzo[10,9,11]-18a-homo-5α-estrane-5,17β-diol 2 g of the compound described under 25h) is dissolved in a shaker in a mixture of 5 ml of tetrahydrofuran and 50 ml of ethyl acetate. 550 mg of palladium on activated carbon (10%) is added, the apparatus is placed under hydrogen and shaken for three hours. Then, it is filtered on Celite and concentrated by evaporation in a vacuum. After purification, 1.69 g of 42a) is obtained.

$^1$H-NMR (CDCl$_3$): δ=5.30 ppm m (1H,Bridge); 4.38 s (1H,OH); 3.85 dd (J=14,7.5 Hz,1H,17-H); 3.50–3.65 m (4H,ketal); 1.04 t (J=7.5 Hz,3H,18a-CH$_3$); 0.98 s (6H,Me-ketal)

b)  5',6'-Dihydro-3,3-[2,2-dimethyl-1,3-propanediyl-bis(oxy)]-5-hydroxy-9H-benzo [10,9,11]-18a-homo-5α-estran-17-one According to general instruction 3), 1.50 g of 42b) is obtained from 1.68 g of the substance described under 42a), 2.35 g of chromium trioxide and 8 ml of pyridine in 70 ml of dichloromethane.

$^1$H-NMR (CDCl$_3$): δ=5.28 ppm m (1H,Bridge); 4.40 s (1H,OH); 3.48–3.60 m (4H,ketal); 1.00 s (3H,Me-ketal); 0.96 s (3H,Me-ketal); 0.76 t (J=7.5 Hz,3H,18a-CH$_3$)

c)  5',6'-Dihydro-3,3-[2,2-dimethyl-1,3-propanediyl-bis(oxy)]-17α-(1-propinyl)-9H-benzo [10,9,11]-18a-homo-5α-estrane-5,17β-diol According to general instruction 2), 1.02 g of 42c) is obtained from 1.35 g of the substance described under 42b), and 19.5 ml of a 1.6 molar solution of n-butyllithium in hexane as well as propine gas.

[α]$_D^{20}$=−78.8° (CHCl$_3$; c=0.510)

$^1$H-NMR (CDCl$_3$): δ=5.31 ppm m (1H,Bridge); 4.44 s (1H,OH); 3.45–3.62 m (4H,ketal); 1.87 s (3H,propine); 1.02 t (J=7.5 Hz,3H,18a-CH$_3$); 0.98 s (3H,Me-ketal); 0.95 s (3 H,Me-ketal)

d)  5',6'-Dihydro-17β-hydroxy-17α-(1-propinyl)-9H-benzo[10,9,11]-18a-homoestr-4-en-3-one According to general instruction 1), 0.99 g of 42c is reacted with 4 n hydrochloric acid in acetone. After purification of the crude product, 421 mg of 42d) is obtained.

Melting point=188°–190° C., [α]$_D^{20}$=+20.3° (CHCl$_3$; c=0.515)

$^1$H-NMR (CDCl$_3$): δ=5.78 ppm sbr (1H,H-4); 5.48 m (1H,Bridge); 1.88 s (3H,propine); 1.05 t (J=7.5 Hz,3H,18a-CH$_3$)

Example 43

17β-Hydroxy-17α-(1-propinyl)-4',5',9,11α-tetrahydro-6'H-benzo[10,9,11]-18a-homo-estr-4-en-3-one a) 3,3-[2,2-Dimethyl-1,3-propanediylbis(oxy)]-4',5',9,11α-tetrahydro-6'H-benzo [10,9,11]-18a-homo-5α-estrane-5,17β-diol 2 g of the compound described under 25h) is dissolved in a shaker in a mixture of 5 ml of tetrahydrofuran and 50 ml of ethyl acetate. 400 mg of platinum(IV) oxide is added, the apparatus is placed under hydrogen and shaken for eight hours. Then, it is filtered on Celite and concentrated by evaporation in a vacuum. After purification, 1.61 g of 43a) is obtained.

$^1$H-NMR (CDCl$_3$): δ=4.28 ppm s (1H,OH); 3.68 ddbr (J=14,7.5 Hz,1H,17-H); 3.46–3.62 m (4H,ketal); 1.02 t (J=7.5 Hz,3H,18a-CH$_3$); 0.95 s (3H,Me-ketal); 0.95 s (3H, Me-ketal)

b) 3,3-[2,2-Dimethyl-1,3-propanediylbis(oxy)]-5-hydroxy-4',5',9,11α-tetrahydro-6'H-benzo [10,9,11]-18a-homo-5α-estran-17-one According to general instruction 3), starting with 1.4 g of the compound described under 43a) and with 1.95 g of chromium trioxide and 6.7 ml of pyridine in 60 ml of dichloromethane, 1.26 g of 43b) is obtained.

$^1$H-NMR (CDCl$_3$): δ=4.30 ppm s (1H,OH); 3.45–3.63 m (4H,ketal); 0.98 s (3H,Me-ketal); 0.96 s (3H,Me-ketal); 0.84 t (J=7.5 Hz, 3H, 18a-CH$_3$)

c) 3,3-[2,2-Dimethyl-1,3-propanediylbis(oxy)]-17α-(1-propinyl)-4',5',9,11α-tetrahydro-6'H-benzo[10,9,11]-18a-homo-5α-estrane-5,17β-diol According to general instruction 2), 761 mg of 43c) is obtained from 1.2 g of the substance described under 43b) and 29 ml of a 1.6 molar solution of n-butyllithium in hexane as well as propine gas.

$[α]_D^{20}$=–5.1° (CHCl$_3$; c=0.505)

$^1$H-NMR (CDCl$_3$): δ=4.34 ppm s (1H,OH); 3.45–3.62 m (4H,ketal); 1.87 s (3H,propine); 1.02 t (J=7.5 Hz,3H,18a-CH$_3$); 0.98 s (3H,Me-ketal); 0.95 s (3H,Me-ketal)

d) 17β-Hydroxy-17α-(1-propinyl)-4',5',9,11α-tetrahydro-6'H-benzo [10,9,11]-18a-homoestr-4-en-3-one According to general instruction 1), 700 mg of 43c) is reacted with 4 n hydrochloric acid in acetone. After purification of the crude product, 463 mg of 43d) is obtained.

$[α]_D^{20}$=+71.7° (CHCl$_3$; c=0.510)

$^1$H-NMR (CDCl$_3$): δ=5.73 ppm sbr (1H,H-4); 1.88 s (3H,propine); 1.06 t (J=7.5 Hz,3H,18a-CH$_3$)

Example 44

5',6'-Dihydro-17α-ethinyl-17β-hydroxy-9H-benzo[10,9,11]-18a-homoestra-4,15-dien-3-one a) 5',6'-Dihydro-3,3-[2,2-dimethyl-1,3-propanediylbis(oxy)]-17-[(trimethylsilyl)oxy]-9H-benzo[10,9,11]-18a-homo-5α-estr-16-en-5-ol According to general instruction 4a), 4.1 g of the substance described under 42b) is reacted with 47 ml of diisopropylamine, 20 ml of a 1.6 molar solution of n-butyllithium in hexane and 5.7 ml of trimethylchlorosilane in absolute tetrahydrofuran. 5.0 g of 44a) is obtained as crude product.

$^1$H-NMR (CDCl$_3$): δ=5.21 ppm m (1H,Bridge); 4.52 m (1H,H-16); 4.35 s (1H,OH); 3.45–3.64 m (4H,ketal); 0.95 s (6H,Me-ketal); 0.83 t (J=7.5 Hz, 3H, 18a-CH$_3$); 0.18 s (9H,Me-Si) b) 5',6'-Dihydro-3,3-[2,2-dimethyl-1,3-propanediylbis(oxy)]-5-hydroxy-9H-benzo [10,9,11]-18a-homo-5α-estr-15-en-17-one According to general instruction 4b), 4.99 g of the compound described under 44a) is reacted with 2.5 g of palladium(II) acetate in acetonitrile. After purification, 3.15 g of 44b) is obtained.

$^1$H-NMR (CDCl$_3$): δ=7.55 ppm dbr (J=6 Hz,1H,H-15); 5.99 dd (J=6.3 Hz,1H,H-16); 5.35 m (1H,Bridge); 4.42 s (1H,OH); 3.45–3.62 m (4H,ketal); 1.00 s (3H,Me-ketal); 1.00 s (3H,Me-ketal); 0.75 t (J=7.5 Hz, 3H, 18a-CH$_3$)

c) 5',6'-Dihydro-3,3-[2,2-dimethyl-1,3-propanediylbis(oxy)]-17α-ethinyl-9H-benzo [10,9,11]-18a-homo-α-estr-15-ene-5,17β-diol According to general instruction 2), 1.2 g of 44b) is reacted with 29 ml of a 1.6 molar solution of n-butyllithium as well as ethine gas in absolute tetrahydrofuran. 1.2 g of 4c) is obtained.

$^1$H-NMR (CDCl$_3$): δ=5.98 ppm dbr (J=6 Hz,1H,H-15); 5.65 dd (J=6.3 Hz,1H,H-16); 5.32 m (1H,Bridge); 4.42 s (1H,OH); 3.45–3.65 m (4H,ketal); 2.62 s (1H,ethine); s 0.98 (3H,Me-ketal); 0.95 s (3H,Me-ketal); 0.82 t (J=7.5 Hz, 3H, 18a-CH$_3$)

d) 5',6'-Dihydro-17α-ethinyl-17β-hydroxy-9H-benzo [10,9,11]-18a-homoestra-4,15-dien-3-one According to general instruction 1), 1.1 g of 44c) is reacted with 4 n hydrochloric acid in acetone. After purification of the crude product, 432 mg of 44d) is obtained.

Melting point=203°–204° C., $[α]_D^{20}$=–89.9° (CHCl$_3$; c=0.500)

$^1$H-NMR (CDCl$_3$): δ=5.98 ppm dbr (J=6 Hz, 1H,H-15); 5.78-sbr (1H,H-4); 5.73 dd (J=6.3 Hz,1H,H-16); 5.47 m (1H,Bridge); 2.65 s (1H,ethine); 0.85 t (J=7.5 Hz,3H,18a-CH$_3$)

Example 45

5',6'-Dihydro-17β-hydroxy-17α-(1-propinyl)-9H-benzo[10,9,11]-18a-homoestra-4,15-dien-3-one a) 5',6'-Dihydro-3,3-[2,2-dimethyl-1,3-propanediylbis(oxy)]-17α-(1-propinyl)-9H-benzo [10,9,11]-18a-homo-5α-estr-15-ene-5,17β-diol According to general instruction 2), 1.2 g of 44b) is reacted with 29 ml of a 1.6 molar solution of n-butyllithium as well as propine gas in absolute tetrahydrofuran. 1.3 g of 5a) is obtained.

$^1$H-NMR (CDCl$_3$): δ=5.92 ppm dbr (J=6 Hz,1H,H-15); 5.62 dd (J=6.3 Hz,1H,H-16); 5.32 m (1H,Bridge); 4.46 s (1H,OH); 3.48–3.64 m (4H,ketal); 1.88 s (3H,propine); 0.97 s (3H,Me-ketal); 0.95 s (3H,Me-ketal); 0.82 t (J=7.5 Hz,3H, 18a-CH$_3$)

b) 5',6'-Dihydro-17β-hydroxy-17α-(1-propinyl)-9H-benzo [10,9,11]-18a-homoestra-4,15-dien-3-one According to general instruction 1), 1.1 g of 45a) is reacted with 4 n hydrochloric acid in acetone. After purification of the crude product by column chromatography on silica gel and subsequent HpLC, 155 mg of 45b) is obtained.

Melting point=210°–217° C., $[α]_D^{20}$=–117.6° (CHCl$_3$; c=0.500)

$^1$H-NMR (CDCl$_3$): δ=5.92 ppm dbr (J=6 Hz,1H,H-15); 5.78 sbr (1H,H-4); 5.70 dd (J=6.3 Hz,1H,H-16); 5.46 m (1H,Bridge ); 1.91 s (3H,propine); 0.84 t (J=7.5 Hz,3H,18a-CH$_3$)

Example 46

3",16β,9,11α-Tetrahydro-6'H-benzo[10, 9,11]cyclopropa [16,17]-18a-homo-19-norpregn-4-ene-3,20-dione a) 9,11α-Dihydro-17β-hydroxy-6'H-benzo[10,9,11]-18a-homoestr-4-en-3-one According to general instruction 1), 7 g of 25h) is reacted with 4 n hydrochloric acid in acetone. After recrystallization of ethyl acetate, 4 g of 46a) is obtained as white crystals.

Melting point=172°–175° C.

¹H-NMR (CDCl₃): δ=5.80 ppm sbr (1H,H-4); 5.75 dbr (J=10 Hz,1H,Bridge); 5.58 m (1H,Bridge); 3.75 ddbr (J=14, 7.5 Hz, 1H, 17-H); 1.08 t (J=7.5 Hz, 3H, 18a-CH₃)

b)  9,11α-Dihydro-3,3-[2,2-dimethyl-1,3-propanediyl-bis(oxy)]-6'H-benzo [10,9,11]-18a-homoestr-5-en-17β-ol 3.98 g of 46a) is reacted analogously to the instructions indicated in example 25c). After purification, 2.59 g of 46b) is obtained as white foam.

$[\alpha]_D^{20}$+7.4° (CHCl₃; c=0.500)

¹H-NMR (CDCl₃): δ=5.70 ppm dbr (J=10 Hz, 1H,Bridge); 5.47 m (1H,Bridge); 5.32 m (1H,H-6); 3.68 m (1H,17-H); 3.42–3.60 m (4H,ketal); 1.06 t (J=7.5 Hz,3H, 18a-CH₃); 1.02 s (3H,Me-ketal); 0.92 s (3 H,Me-ketal)

c)  9,11α-Dihydro-3,3-[2,2-dimethyl-1,3-propanediyl-bis(oxy)]-6'H-benzo [10,9,11]-18a-homoestr-5-en-17-one According to general instruction 3), 2.55 g of 46c) is obtained as white crystals from 2.57 g of the substance described under 46b), 3.74 g of chromium trioxide and 13 ml of pyridine in 110 ml of dichloromethane.

Melting point=190° C.

¹H-NMR (CDCl₃): δ=5.62 ppm dbr (J=10 Hz, 1H,Bridge); 5.48 m (1H,Bridge); 5.35 m (1H,H-6); 3.42–3.62 m (4H,ketal); 1.04 s (3H,Me-ketal); 0.92 s (3H, Me-ketal); 0.78 t (J=7.5 Hz, 3H, 18a-CH₃)

d)  9,11α-Dihydro-3,3-[2,2-dimethyl-1,3-propanediyl-bis(oxy)]-17-[[(1,1,2,2,3,3,4,4,4-nonafluorobutyl)sulfonyl] oxy]-6'H-benzo [10,9,11]-18a-homoestra-5,16-diene 2.54 g of the substance described under 46c) is dissolved in 30 ml of absolute tetrahydrofuran. A solution of 3.11g of potassium-bis(trimethylsilyl)amide in 15 ml of absolute 1,2-dimethoxyethane and 1.45 ml of perfluorobutanesulfonyl fluoride are added. Then, it is allowed to stir for 5 more hours at room temperature and then aqueously worked up (B, F). After purification, 1.73 g of 46d) is obtained.

¹H-NMR (CDCl₃): δ=5.60 ppm m (2H,H-16 and Bridge); 5.50 m (1H,Bridge); 5.35 m (1H,H-6); 3.42–3.60 m (4H, ketal); 1.02 s (3H,Me-ketal); 0.92 s (3 H, Me-ketal); 0.89 t (J=7.5 Hz, 3H, 18a-CH₃)

e)  9,11α-Dihydro-3,3-[2,2-dimethyl-1,3-propanediyl-bis(oxy)]-6'H-benzo[10,9,11]-18a-homo-19-norpregna-5, 16-dien-20-one 1.7 g of the compound described under 46d) is dissolved in 32 ml of absolute dimethylformamide and mixed with 1.25 ml of (1-ethoxyvinyl)tributyltin, 320 mg of anhydrous lithium chloride, 27 mg of palladium(II) acetate and 65 mg of triphenylphosphine. It is heated for 5 hours to 60° C. and then for 20 minutes to 100° C. After aqueous working up (B, F) and purification, 682 mg of 46e) is obtained.

Melting point=165°–168° C.

¹H-NMR (CDCl₃): δ=6.81 ppm dd (J=3.2 Hz,1H,H-16); 5.68 m (1H,Bridge); 5.46 m (1H,Bridge); 5.36 m (1H,H-6); 3.40–3.63 m (4H,ketal); 2.28 s (3H,acetyl); 1.02 s (3H,Me-ketal); 0.90 s (3H,Me-ketal); 0.73 t (J=7.5 Hz,3H,18a-CH₃)

f)  3",16β,9,11α-Tetrahydro-3,3-[2,2-dimethyl-1,3-propanediylbis(oxy)]-6'H-benzo [10,9,11]cyclopropa [16,17 ]-18a-homo-19-norpregn-5-en-20-one 78 mg of an 80% suspension of sodium hydride in mineral oil is added to a suspension of 670 mg of trimethylsulfoxonium iodide in 8.5 ml of dimethyl sulfoxide. It is allowed to stir for 90 more minutes at room temperature and then a suspension of 672 mg of the compound, described under 46e), in 2.8 ml of dimethyl sulfoxide is added. Then, it is allowed to stir for 10 more hours at room temperature and then aqueously worked up (A, F). After purification, 168 mg of 46f) is obtained.

¹H-NMR (CDCl₃): δ=5.64 ppm dbr (J=10 Hz, 1H,Bridge); 5.45 m (1H,Bridge); 5.33 m (1H,H-6); 3.40–3.61 m (4H,ketal); 2.03 s (3H, acetyl); 1.00 s (3H,Me-ketal); 0.92 s (3H,Me-ketal); 0.73 t (J=7.5 Hz,3H,18a-CH₃)

g)  3",16β,9,11α-Tetrahydro-6'H-benzo[10,9,11]cyclopropa[16,17]-18a-homo-19-norpregn-4-ene-3,20-dione 154 mg of 46f) is dissolved in 8 ml of acetone, mixed with 0.18 ml of 2n hydrochloric acid and the mixture is stirred for 5.5 hours at room temperature. After aqueous working up (B, F), the crude product is purified by column chromatography on silica gel and subsequent HpLC and 36 mg of 46g) is obtained.

¹H-NMR (CDCl₃): δ=5.82 ppm sbr (1H,H-4); 5.68 dbr (J=10 Hz,1H,Bridge); 5.56 m (1H,Bridge); 2.54 m (1H,H-11); 2.03 s (3H,acetyl); 0.78 t (J=7.5 Hz,3H,18a-CH₃)

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. 19,11-Bridged 4-estrenes of general formula I

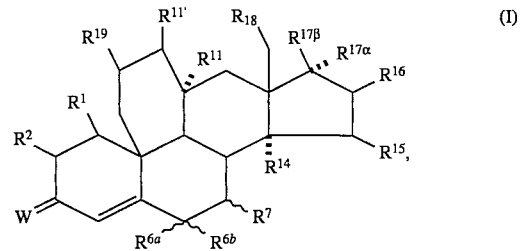

in which

W is an oxygen atom;

R¹ and R² are each a hydrogen atom or together form an additional bond or form a methylene bridge in α-position;

R⁶ᵃ and R⁶ᵇ are each a hydrogen atom or together form a methylene group or together form a three-membered ring with carbon atom 6, and R⁷ is a hydrogen atom; or R⁶ᵃ is a hydrogen atom or a fluorine, chlorine, bromine or iodine atom or a straight-chain or branched-chain, saturated alkyl radical in the α- or β-position with up to 4 carbon atoms, and R⁶ᵇ and R⁷ are each a hydrogen atom or together form an additional bond; or R⁶ᵇ and R⁷ together are a methylene bridge in the α- or β-position, and R⁶ᵃ is a hydrogen atom;

R⁷ is a straight-chain or branched-chain, saturated alkyl radical in the α- or β-position with up to 4 carbon atoms or a thio group —SR²⁰, in which R²⁰ is a hydrogen atom or an alkanoyl group with 1to 4 carbon atoms;

R¹⁴, R¹⁵ and R¹⁶ are each a hydrogen atom; or

R¹⁴ is a hydrogen atom in the α-position and R¹⁵ and R¹⁶ together form an additional bond or form a methylene bridge in the α- or β-position; or R¹⁴ and R¹⁵ are each a hydrogen atom and R¹⁶ is a C₁₋₄-alkyl group in the αor β-position; or R¹⁶ together with R¹⁷ᵅ form a methylene bridge in the α-position and R¹⁷ᵝ is a group $$-\underset{\underset{O}{\|}}{C}-R^{22};$$

or

R$^{16}$ is a hydrogen atom and R$^{14}$ and R$^{15}$ together form an additional bond;

R$^{11}$, R$^{11'}$ and R$^{19}$ are each a hydrogen atom; or

R$^{11}$ is a hydrogen atom in the α-position, and R$^{11'}$ and R$^{19}$ together form an additional bond; or R$^{19}$ is a hydrogen atom and R$^{11}$ and R$^{11'}$ together form an additional bond, R$^{17β}$/R$^{17α}$ are the following combinations:

$$-OR^{21}/-(CH_2)_n-A,$$

$$-OR^{21}/-(CH_2)_m-C{\equiv}C-B,$$

$$-OR^{21}/-(CH_2)_p-CH{=}CH-(CH_2)_k-D,$$

$$-OR^{21}/-HC{=}C{=}CEG,$$

$$-OR^{21}/-CF_3,$$

$$-\underset{\underset{O}{\|}}{C}-R^{22}/-OR^{23},$$

$$-\underset{\underset{O}{\|}}{C}-R^{22}/-C_{1\text{-}4}\text{-alkyl, or}$$

$$-\underset{\underset{O}{\|}}{C}-R^{22}/-F;$$

R$^{21}$ and R$^{23}$ are each a hydrogen atom, a C$_{1\text{-}4}$-alkyl or a C$_{1\text{-}4}$-alkanoyl group;

R$^{22}$ is a C$_{1\text{-}3}$-alkyl group;

A is a hydrogen atom, a cyano group, —COOR$^{24}$ or —OR$^{25}$ in which R$^{24}$ is C$_{1\text{-}4}$-alkyl and R$^{25}$ is hydrogen, C$_{1\text{-}4}$-alkyl or C$_{1\text{-}4}$-alkanoyl;

B is a hydrogen atom; a C$_{1\text{-}4}$-alkyl group; a C$_2$- or C$_3$-alkinyl group; a fluorine, chlorine, bromine or iodine atom; a hydroxyalkyl, alkoxyalkyl or alkanoyloxyalkyl group with 1 to 4 carbon atoms each in the alkyl, alkoxy or alkanoyloxy part;

D is a hydrogen atom, a hydroxy, C$_{1\text{-}4}$-alkoxy or C$_{1\text{-}4}$-alkanoyloxy group;

E and G are each hydrogen or C$_{1\text{-}3}$-alkyl;

n is 0, 1, 2, 3 or 4;

m is 0, 1 or 2;

p is 0 or 1;

k is 0, 1, 2 or 3; and

R$^{18}$ is a hydrogen atom or a methyl group.

2. 19,11-Bridged 4-estrenes according to claim 1, wherein R$^{6a}$ and R$^{6b}$ are each a hydrogen atom or together form a three-membered ring with carbon atom 6.

3. 19,11-Bridged 4-estrenes according to claim 1, wherein R$^{6a}$ is a chlorine or bromine atom or a straight-chain, saturated C$_{1\text{-}4}$-alkyl radical in the α- or β-position.

4. 19,11-Bridged 4-estrenes according to claim 1, wherein R$^{6b}$ and R$^7$ together form a methylene bridge in α- or the β-position or a double bond.

5. 19,11-Bridged 4-estrenes according to claim 1, wherein R$^7$ is a straight-chain or branched-chain, saturated alkyl radical in the α- or β-position with up to 4 carbon atoms.

6. 19,11-Bridged 4-estrenes according to claim 1, wherein R$^{14}$, R$^{15}$ and R$^{16}$ are each a hydrogen atom.

7. 19,11-Bridged 4-estrenes according to claim 1, wherein R$^{14}$ is a hydrogen atom in the α-position, and R$^{15}$ and R$^{16}$ together form an additional bond or form a methylene bridge in the β-position.

8. 19,11-Bridged 4-estrenes according to claim 1, wherein R$^{17β}$/R$^{17α}$ are the following combinations:

—OH/—CH$_3$,

—OC(O)CH$_3$/—CH$_3$,

—OH/—C≡CH,

—OC(O)CH$_3$/—C≡CH,

—OH/—C≡C—CH$_3$,

—OC(O)CH$_3$/—C≡C—CH$_3$,

—C(O)CH$_3$/—OC(O)CH$_3$.

9. A pharmaceutical preparation, comprising a compound of general formula I according to claim 1 and a pharmaceutically compatible vehicle.

10. The compounds:

17-(Acetyloxy)-9,11α-dihydro-6'H-benzo[10,9,11]-19-norpregn-4-ene-3,20-dione;

17-(acetyloxy)-9,11α-dihydro-6-methyl-6'H-benzo[10,9,11]-19-norpregna-4,6-diene-3,20-dione;

17-(acetyloxy)-9,11α-dihydro-6α-methyl-6'H-benzo[10,9,11]-19-norpregn-4-ene-3,20-dione;

17-(acetyloxy)-6-chloro-9,11α-dihydro-6'H-benzo[10,9,11]-19-norpregna-4,6-diene-3,20-dione;

17-(acetyloxy)-6-chloro-1β,2β,9,11α-tetrahydro-3'H-cyclopropa[1,2][6"H]benzo[10,9,11]-19-norpregna-4,6-diene-3,20-dione;

17-(acetyloxy)-4',5',9,11α-tetrahydro-6'H-benzo[10,9,11]-19-norpregn-4-ene-3,20-dione;

17-(acetyloxy)-6-methyl-4',5',9,11α-tetrahydro-6'H-benzo[10,9,11]-19-norpregna-4,6-diene-3,20-dione;

17-(acetyloxy)-6-chloro-1β,2β,4",5",9,11α-hexahydro-3'H-cyclopropa[1,2][6"H]benzo[10,9,11]-19-norpregn-4-ene-3,20-dione;

17-(acetyloxy)-5',6'-dihydro-6-methyl-9H-benzo[10,9,11]-19-norpregna-46-diene-3,20-dione;

17-(acetyloxy)-5',6'-dihydro-9H-benzo[10,9,11]-19-norpregn-4-ene-3,20-dione;

17-(acetyloxy)-9,11α-dihydro-6'H-benzo[10,9,11]-18a-homo-19-norpregn-4-ene-3,20-dione;

17-(acetyloxy)-9,11α-dihydro-6-methyl-6'H-benzo[10,9,11]-18a-homo-19-norpregna-4,6-diene-3,20-dione;

9,11α-dihydro-17-methyl-6'H-benzo[10,9,11]-19-norpregn-4-ene-3,20-dione;

17-(acetyloxy)-9,11α-dihydro-6'H-benzo[10,9,11]-19-norpregna-4,6-diene-3,20-dione;

3',9,11α,16β-tetrahydrocyclopropa[16,17][6H]benzo-[10,9,11 ]-19-norpregn-4-ene-3,20-dione;

9,11α-dihydro-17-methyl-6'H-benzo[10,9,11]-18a-homo-19-norpregn-4-ene-3,20-dione;

3',9,11α,16β-tetrahydrocyclopropa[16,17][6H]-benzo[10,9,11]-18a-homo-19-norpregn-4-ene-3,20-dione;

9,11α,-dihydro-17β-hydroxy-17α-methyl-6'H-benzo[10,9,11]estr-4-en-3-one;

9,11α-dihydro-17α-ethinyl-17β-hydroxy-6'H-benzo[10,9,11]estr-4-en-3-one;

9,11α-dihydro-17β-hydroxy-17α-(1-propinyl)-6'H-benzo[10,9,11]estr-4-en-3-one;

9,11α-dihydro-17β-hydroxy-17α-[1,3-pentadiinyl]-6'H-benzo[10,9,11]estr-4-en-3-one;

(Z)-9,11α-dihydro-17β-hydroxy-17α-(3-hydroxy-1-propyl)-6'H-benzo[10,9,11]estr-4-en-3-one;

9,11α-dihydro-17β-hydroxy-17α-(3-hydroxypropyl)-6'H-benzo[10,9,11]estr-4-en-3-one;

17β-hydroxy-17α-methyl-4',5',9,11α-tetrahydro-6'H-benzo[10,9,11]estr-4-en-3-one;

17α-ethinyl-17β-hydroxy-4',5',9,11α-tetrahydro-6'H-benzo[10,9,11]estr-4-en-3-one;

17β-hydroxy-17α-(1-propinyl)-4',5',9,11α-tetrahydro-6'H-benzo[10,9,11]estr-4-en-3-one;

5',6'-dihydro-17α-ethinyl-17β-hydroxy-9H-benzo[10,9,11]estr-4-en-3-one;

5',6'-dihydro-17β-hydroxy-17α-(1-propinyl)-9H-benzo[10,9,11]estr-4-en-3-one;

9,11α-dihydro-17α-ethinyl-17β-hydroxy-6'H-benzo[10,9,11]-18a-homoestr-4-en-3-one;

9,11α-dihydro-17β-hydroxy-17α-(1-propinyl)-6'H-benzo[10,9,11]-18a-homoestr-4-en-3-one;

17α-(1-butinyl)-9,11α-dihydro-17β-hydroxy-6'H-benzo[10,9,11]-18a-homoestr-4-en-3-one;

9,11α-dihydro-17α-(1,2-propadienyl)-17β-hydroxy-6'H-benzo[10,9,11]-18a-homoestr-4-en-3-one;

17α-ethinyl-17β-hydroxy-4',5',9,11α-tetrahydro-6'H-benzo[10,9,11]18a-homoestr-4-en-3-one;

17β-hydroxy-17α-(1-propinyl)-4',5',9,11α-tetrahydro-6'H-benzo[10,9,11]-18a-homoestr-4-en-3-one;

5',6'-dihydro-17α-ethinyl-17β-hydroxy-9H-benzo[10,9,11]-18a-homoestr-4-en-3-one;

5',6'-dihydro-17β-hydroxy-17α-(1-propinyl)-9H-benzo[10,9,11]-18a-homoestr-4-en-3-one;

9,11α-dihydro-17α-ethinyl-17β-hydroxy-6'H-benzo[10,9,11]estra-4,15-dien-3-one;

9,11-dihydro-17β-hydroxy-17α-(1-propinyl)-6'H-benzo[10,9,11]estra-4,15-dien-3-one;

17α-ethinyl-17β-hydroxy-4',5',9,11α-tetrahydro-6'H-benzo[10,9,11]estra-4,15-dien-3-one;

5',6'-dihydro-17α-ethinyl-17β-hydroxy-9H-benzo[10,9,11]estra-4,15-dien-3-one;

5',6'-dihydro-17β-hydroxy-17α-(1-propinyl)-9H-benzo[10,9,11]estra-4,15-dien-3-one;

9,11α-dihydro-17α-ethinyl-17β-hydroxy-6'H-benzo[10,9,11]-18a-homoestra-4,15-dien-3-one;

9,11α-dihydro-17β-hydroxy-17α-(1-propinyl)-6'H-benzo[10,9,11]-18a-homoestra-4,15-dien-3-one;

17α-ethinyl-17β-hydroxy-4',5',9,11α-tetrahydro-6'H-benzo[10,9,11]-18a-homoestra-4,15-dien-3-one;

5',6'-dihydro-17α-ethinyl-17β-hydroxy-9H-benzo[10,9,11]-18a-homoestra-4,15-dien-3-one;

5',6'-dihydro-17β-hydroxy-17α-(1-propinyl)-9H-benzo[10,9,11]-18a-homoestra-4,15-dien-3-one;

4",5',9,11α-tetrahydrospiro[6'H-benzo[10,9,11]estr-4-ene-17β,2"(3"H)-furan]-3-one;

3",4",9,11α-tetrahydrospiro[6'H-benzo[10,9,11]estr-4-ene-17β,2"(5"H)-furan]-3,5"-dione;

3"",4"",6α,7α,9,11α,15α,16α-octahydrospiro[3'H,3"H-dicyclopropa[6,7:15,16]-[6H]benzo[10,9,11]estr-4-ene-17β,2""(5""H)-furan]-3,5""-dione;

3"",4"",9',11'α,15'α,16'α-hexahydrospiro[cyclopropane-1,6'-[3H]cyclopropane[15,16][6H]benzo-[10,9,11]estr-4-ene-17'β,2""(5"")-furan]-3',5""-dione;

3"",4"",9',11',15'α,16'α-hexahydrospiro-[cyclopropane-1,6'-[3H]cyclopropane[15,16][6H]benzo-[10,9,11]estra-1,4-diene-17'β,2""(5""H)-furan]-3',5""-dione;

3"",4"",4"',5"',6α,7α,9,11α,15α,16α-decahydrospiro[3'H,3"H-dicyclopropa[6,7:15,16][6H]benzo-[10,9,11]estr-4-ene-17β,2""(5""H)-furan]-3,5""-dione;

3",4",9,11α-tetrahydrospiro[5'H-benzo[10,9,11]-18a-homoestr-4-ene-17β,2"(5")-furan]-3,5"-dione;

3"",4"",6α,7α,9,11α,15α,16α-octahydrospiro[3'H,3"H-dicyclopropa[6,7:15,16][6H]benzo[10,9,11]-18a-homoestr-4-ene-17β,2""(5""H)-furan]-3,5""-dione;

9,11α-dihydro-17α-ethinyl-6'H-benzo[10,9,11]estr-4-en-17β-ol;

17α-ethinyl-4',5',9,11α-tetrahydro-6'H-benzo[10,9,11]estr-4-en-17β-ol;

5',6'-dihydro-17α-ethinyl-9H-benzo[10,9,11]estr-4-en-17β-ol;

9,11α-dihydro-17α-ethinyl-6'H-benzo[10,9,11]estra-4,15-dien-17β-ol;

9,11α-dihydro-17α-ethinyl-6'H-benzo[10,9,11]-18a-homoestr-4-en-17β-ol;

9,11α-dihydro-17α-ethinyl-6'H-benzo[10,9,11]-18a-homoestra-4,15-dien-17β-ol.

* * * * *